United States Patent
Weerasooriya et al.

(10) Patent No.: US 12,338,382 B2
(45) Date of Patent: Jun. 24, 2025

(54) SURFACTANTS HAVING NON-CONVENTIONAL HYDROPHOBES

(71) Applicants: HARCROS CHEMICALS, INC., Kansas City, KS (US); BOARD OF REGENTS, THE UNIVERSITY OF TEXAS SYSTEM, Austin, TX (US)

(72) Inventors: Upali Weerasooriya, Austin, TX (US); Peter Radford, Lenexa, KS (US); Kevin Sikkema, Overland Park, KS (US); John Boorem, Kansas City, KS (US); Aaron Boorem, Leavenworth, KS (US); Kurt Cheshire, Shawnee, KS (US); Kishore K. Mohanty, Austin, TX (US); Krishna Panthi, Cedar Park, TX (US); Himanshu Sharma, Austin, TX (US); Pinaki Ghosh, Austin, TX (US)

(73) Assignee: Harcros Chemicals, Inc., Kansas City, MO (US)

( * ) Notice: Subject to any disclaimer, the term of this patent is extended or adjusted under 35 U.S.C. 154(b) by 473 days.

(21) Appl. No.: 16/500,250

(22) PCT Filed: Apr. 4, 2018

(86) PCT No.: PCT/US2018/026073
§ 371 (c)(1),
(2) Date: Oct. 2, 2019

(87) PCT Pub. No.: WO2018/187463
PCT Pub. Date: Oct. 11, 2018

(65) Prior Publication Data
US 2021/0039060 A1  Feb. 11, 2021

Related U.S. Application Data

(60) Provisional application No. 62/481,393, filed on Apr. 4, 2017.

(51) Int. Cl.
*C09K 23/00* (2022.01)
*C07C 59/125* (2006.01)
(Continued)

(52) U.S. Cl.
CPC .......... *C09K 23/00* (2022.01); *C07C 59/125* (2013.01); *C07C 217/28* (2013.01);
(Continued)

(58) Field of Classification Search
None
See application file for complete search history.

(56) References Cited

U.S. PATENT DOCUMENTS 3,485,879 A    12/1969  Mameniskis et al.
3,906,027 A *  9/1975  Meussdoerffer ... C08G 65/3348
                                                       560/12

(Continued)

FOREIGN PATENT DOCUMENTS

GB    2088863 A  *  6/1982  .......... C07C 59/125
JP    59069135 A  *  4/1984

(Continued)

OTHER PUBLICATIONS

JP-59069135-A Eng Translation (Year: 1984).*

(Continued)

*Primary Examiner* — Jeffrey D Washville
(74) *Attorney, Agent, or Firm* — Stinson LLP

(57) ABSTRACT

The present invention is directed to surfactants with small hydrophobes, which are of non-conventional hydrophobe size. The surfactants of the present invention utilize a small hydrophobic moiety with a polyalkoxylate chain comprising PO, BO and/or EO groups, with optional ionic groups, such as anionic, cationic and zwitterionic, to achieve the desired hydrophilic-lipophilic balance (HLB). The present invention is further directed to formulations comprising the surfactants (Continued)

of the invention, and methods of using the surfactants of the invention, including in enhanced oil recovery applications.

18 Claims, 21 Drawing Sheets

(51) Int. Cl.
| | |
|---|---|
| C07C 217/28 | (2006.01) |
| C07C 305/10 | (2006.01) |
| C09K 8/584 | (2006.01) |
| C09K 23/16 | (2022.01) |
| C09K 23/42 | (2022.01) |
| C11D 1/06 | (2006.01) |
| C11D 1/29 | (2006.01) |
| C11D 1/722 | (2006.01) |
| C11D 11/00 | (2006.01) |
| E21B 43/16 | (2006.01) |

(52) U.S. Cl.
CPC .......... *C07C 305/10* (2013.01); *C09K 8/584* (2013.01); *C09K 23/16* (2022.01); *C11D 1/06* (2013.01); *C11D 1/29* (2013.01); *C11D 1/722* (2013.01); *E21B 43/16* (2013.01); *C11D 2111/20* (2024.01)

(56) References Cited

U.S. PATENT DOCUMENTS

| | | | |
|---|---|---|---|
| 5,484,597 A | 1/1996 | Schenker et al. | |
| 5,990,206 A | 11/1999 | Tanaka et al. | |
| 6,562,875 B1 * | 5/2003 | Corbel ............... | B01D 19/0404 516/134 |
| 9,862,877 B2 | 1/2018 | Weerasooriya et al. | |
| 2009/0124525 A1 | 5/2009 | Futterer et al. | |
| 2009/0186981 A1 * | 7/2009 | Thetford ............... | C09D 7/45 524/592 |
| 2010/0184603 A1 * | 7/2010 | Stoesser ............. | C08G 65/2603 504/362 |
| 2011/0190175 A1 * | 8/2011 | Steinbrenner ......... | C09K 8/584 507/259 |
| 2012/0252987 A1 | 10/2012 | Peretolchin et al. | |
| 2013/0281327 A1 * | 10/2013 | Weerasooriya ........ | C09K 8/584 562/587 |
| 2014/0100318 A1 * | 4/2014 | Park ...................... | C08G 81/00 524/451 |
| 2014/0209322 A1 | 7/2014 | Francis et al. | |
| 2015/0105301 A1 * | 4/2015 | Weerasooriya .......... | C11D 1/06 507/261 |
| 2015/0291872 A1 * | 10/2015 | Fernandez .............. | E21B 43/26 166/308.1 |
| 2016/0152883 A1 * | 6/2016 | Fernandez ............... | C09K 8/64 507/136 |
| 2016/0264847 A1 | 9/2016 | Weerasooriya et al. | |
| 2017/0334840 A1 | 11/2017 | Weerasooriya et al. | |

FOREIGN PATENT DOCUMENTS

| | | | | |
|---|---|---|---|---|
| JP | 11228198 A | * | 8/1999 | .......... C04B 24/166 |
| JP | 3339907 B2 | * | 10/2002 | |
| JP | 3993679 B2 | * | 10/2007 | ............. C04B 24/16 |
| WO | 2012/002738 A | | 1/2012 | |
| WO | WO 2012/154376 A2 | | 11/2012 | |
| WO | WO 2014/139027 A1 | | 9/2014 | |
| WO | WO 2015/138444 A1 | | 9/2015 | |
| WO | WO 2018/187463 A1 | | 10/2018 | |
| WO | WO 2019/195604 A1 | | 10/2019 | |
| WO | WO 2019/195606 A1 | | 10/2019 | |

OTHER PUBLICATIONS

JP-11228198-A translation (Year: 1998).*
JP-11228198-A Eng trans (Year: 1998).*
JP-3993679-B2 Eng trans (Year: 1999).*
JP 3339907 Eng trans (Year: 2002).*
International Search Report and Written Opinion dated Jul. 20, 2018 for related application PCT/US2018/026073 (16 pgs).
International Search Report and Written Opinion dated Aug. 1, 2019 for application PCT/US2019/025873 (9 pgs).
International Search Report and Written Opinion dated Aug. 7, 2019 for application PCT/US2019/025871 (9 pgs).
English Language Translation of Japanese Patent Application Publication No. S59-69315, 4 pages.
Wu et al., "Effect of EO and PO positions in nonionic surfactants on surfactant properties and demulsification performance", Colloids and Surfaces A:Physicochem. Eng. Aspects 252, Jan. 3, 2005, (13 pgs).
Bahadur, P., "Block copolymers - Their microdomain formulation (in solid tate) and surfactant behaviour (in solution)", Current Science, vol. 80, No. 8, Apr. 25, 2001, pp. 1002-1007 (6 pgs).

* cited by examiner

SURFACTANTS HAVING NON-CONVENTIONAL HYDROPHOBES

CROSS-REFERENCE TO RELATED APPLICATIONS

This application is based on and claims priority to U.S. Provisional Application Ser. No. 62/481,393 filed on Apr. 4, 2017, which is incorporated herein by reference in its entirety.

BACKGROUND OF THE INVENTION

1. Field of the Invention

The invention is directed to the field of surfactants, which are suitable for enhanced oil recovery and other surfactant applications.

2. Description of Related Art

A large amount of oil is left unrecovered from oil reservoirs after primary and secondary floods due to various reasons. Among these factors, high capillary forces (between oil and water) are largely responsible for trapping of oil in the porous media. Surfactants that can lower the interfacial tension (IFT) with oil have traditionally been studied to improve the oil recovery. Studies have shown that a significant improvement in oil recovery can be achieved by injecting suitable surfactants in the reservoir, which in turn results in a significant reduction of capillary forces and mobilization of trapped oil. However, traditionally used surfactants suffer from severe limitations due to their limited applicability in a high salinity/hardness and a high temperature environment. These surfactants tend to be unstable (not soluble) under these conditions and therefore cannot be used for improving the oil recovery.

In addition to an ultralow interfacial tension, a favorable microemulsion rheology is critical in lowering the surfactant requirement. Co-solvents have shown to lower the microemulsion viscosity, lower surfactant retention and improve the oil recovery. Alkali co-solvent polymer (ACP) floods have been developed recently for acidic crude oils, employing in-situ generated Naphthenic soap as the surfactant.

A surfactant is a surface-active compound that can lower the interfacial tension between two phases by acting as the bridge between the interfaces. A surfactant consists of a hydrophilic head (which prefers the aqueous phase) and a lipophilic tail (which prefers an organic or gas phase). The hydrophilic-lipophilic balance (HLB) determines the solubility of surfactants in aqueous or organic (oil) phases. Anionic surfactants have been used for surfactant floods because these surfactants have shown to lower the interfacial tension with oil-brine system to ultralow values ($10^{-3}$ dynes/cm). Traditionally used anionic surfactants include alkyl benzene sulfonates (ABS), alpha olefin sulfonates (AOS), internal olefin sulfonates (IOS) and alcohol sulfates. These surfactants show limited stability (solubility) at high temperature/salinity/hardness environment. In addition, these surfactants are not suitable for crude oils with high equivalent alkane carbon numbers (EACN). Large hydrophobe alcohol alkoxy carboxylates and alcohol alkoxy sulfates, typically longer than $C_{11-12}$, were developed as the main hydrophobe. The addition of propylene oxide (PO) and ethylene oxide (EO) groups was performed to achieve higher performance and better tolerance at high temperature and salinity (hardness) conditions.

BRIEF SUMMARY OF THE INVENTION

In one aspect of the invention, surfactants of the present invention generally have the formula:

$$X\text{-}((A^1_x\text{-}A^2_y)\text{-}Y)_n \qquad (I)$$

wherein X is an alcohol, an amine, or an alkyl- or alkoxy-amine having from 1 to 8 total carbons; one of $A^1$ and $A^2$ is PO, butylene oxide (BO) and/or a combination of PO and BO, and the other of $A^1$ and $A^2$ is EO, and independent $A^1$ and $A^2$ groups may be in blocks and/or in random order; x or y are 7-100 when $A^1$ or $A^2$, as applicable, is PO or BO; x or y are 0-250 when $A^1$ or $A^2$, as applicable, is EO; n is 1 to 4 or 1 to 3; Y is an ionic group, a zwitterionic group or H; and PO is —$CH_2CH(CH_3)$—O—, BO is —$CH_2CH(CH_2CH_3)$—O— or —$CH_2CH_2CH(CH_3)$—O— and EO is —$CH_2$—$CH_2$—O—.

In one aspect of the invention, alkoxy polyalkoxylate surfactants of the present invention have the formula:

$$R^1\text{—}O\text{-}(A^1_x\text{-}A^2_y)\text{-}Z \qquad (II)$$

wherein $R^1$ is $C_1$ to $C_8$ alkyl; $A^1$, $A^2$, x, and y are as defined in formula (I); and Z is an ionic group or H.

In one aspect of the invention, polyol alkoxylate surfactants of the invention have the formula:

$$R^1_a\text{—}CH_b\text{—}(CH_2\text{—}O\text{-}(A^1_x\text{-}A^2_y)\text{-}Z)_n,$$

wherein a+b+n=4; a=0-3; b=0-3; n=1-4; $R^1$ is $C_1$ to $C_6$ alkyl; $A^1$, $A^2$, x, or y is as described above with respect to formula (I); and Z is an ionic group or H. In certain embodiments, the total carbon atoms in a $R^1_a$—$CH_b$—($CH_2$—O—$)_n$ group is equal to or less than 8.

In one aspect of the invention, polyol alkoxylate surfactants of the invention have the following formula:

$$\text{polyol-}((A^1_x\text{-}A^2_y)Z)_n \qquad (IV)$$

wherein one or more of the hydrogen molecules of one or more hydroxyl groups of the polyol is replaced with $(A^1_x\text{-}A^2_y)Z$; $A^1$, $A^2$, x, and y are as described above with respect to formula (I); Z is an ionic group or H; and n is equal to or less than the total number of hydroxyl groups on the polyol, such that not all of the hydroxyl groups are alkoxylated.

In one aspect of the invention, amine, alkoxyamine and alkylamine polyalkoxylate surfactants of the invention have the formula:

$$R^1_a\text{—}NH_m((R^3O)_d(A^1_x\text{-}A^2_y)Y)_n \qquad (V)$$

wherein a+m+n=3; a=0-2; m=0-2; d=0-1; n=1-3; $R^3$ and $R^1$ are independently $C_1$ to $C_8$ alkyl, with a combined total of 8 or fewer carbons; $A^1$, $A^2$, x, and y are as described above with respect to formula (I); and Y is H, an ionic group, a zwitterionic group, or a cationic when the nitrogen atom is quaternary, with a positive charge, and a negatively charged anion as a counterion.

In one aspect of the invention, polyamine polyalkoxylate surfactants of the invention have the formula:

$$\text{polyamine-}((A^1_x\text{-}A^2_y)Y)_n \qquad (VI)$$

wherein one or more polyalkoxy groups $(A^1_x\text{-}A^2_y)Y$ are attached to one or more of the nitrogen atoms of the polyamine, and $A^1$, $A^2$, x, and y are as described above with respect to formula (I); Y is H, an ionic group, a zwitterionic group, or a cationic when the nitrogen atom is quaternary, with a positive charge, and a negatively charged anion as a counterion; and n is equal to or less than the number of displaceable hydrogens on the nitrogen atoms.

Another aspect of the invention, is directed to an aqueous composition comprising a compound described herein, for example a compound of formula (I), (II), (III), (IV), (V) or (VI). Another aspect of the invention is directed to an emulsion comprising such aqueous composition and a hydrocarbon material.

Another aspect of the invention is directed to a method of using a compound described herein, for example a compound of formula (I), (II), (III), (IV), (V) or (VI), in an enhanced oil recovery method comprising contacting a hydrocarbon with the compound when the hydrocarbon is in contact with a solid material in a petroleum reservoir and allowing the hydrocarbon material to separate from the solid material. Another aspect of the invention is directed to a method of using a compound described herein, for example a compound of formula (I), (II), (III), (IV), (V) or (VI) in household, institutional or industrial cleaning comprising contacting a household, institutional or industrial surface with the compound.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENT

Figure 1:
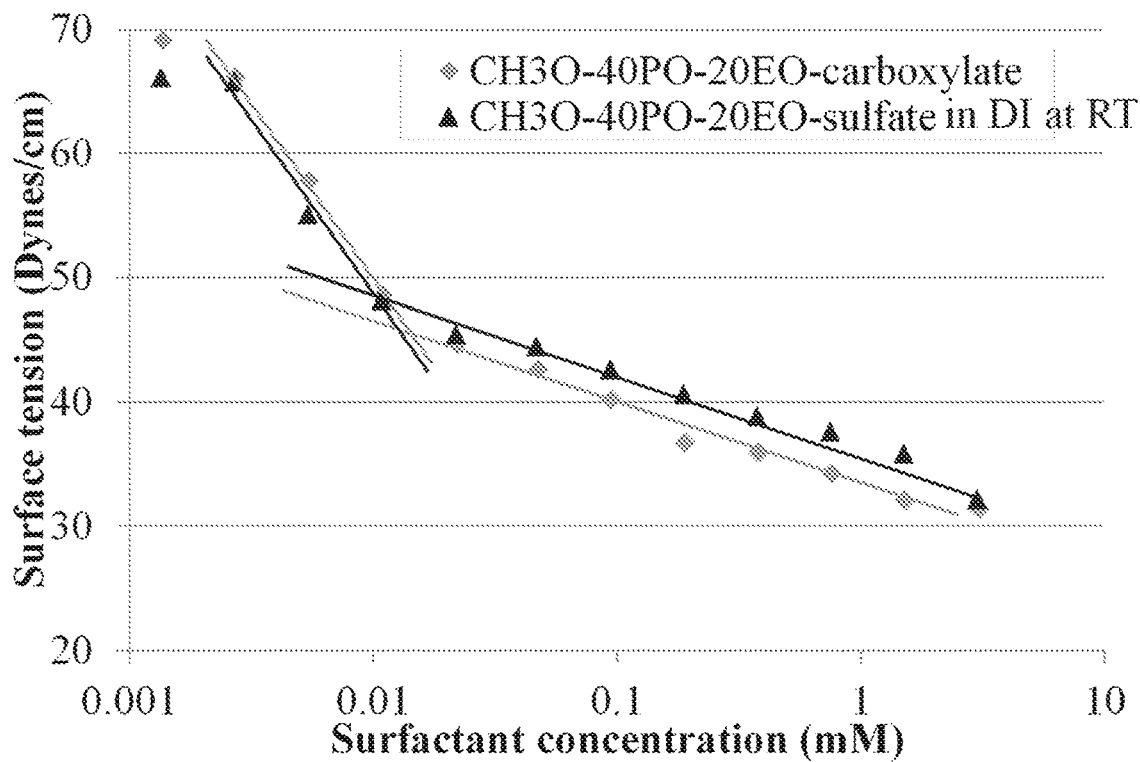
FIG. 1 depicts surface tension measurements of $CH_3O$-40PO-20EO-carboxylate and $CH_3O$-40PO-20EO-sulfate.

The present invention is directed to surfactants with smaller hydrophobes, which are of non-conventional hydrophobe size, and are herein referred to as non-conventional hydrophobes. Conventional hydrophobes are sometimes referred to as "hard" hydrophobes, i.e. a compound that shows no compatibility with water. Unlike prior art surfactants that incorporate a hard hydrophobe, the surfactants of the present invention utilize a small hydrophobic moiety with a polyalkoxylate chain. In addition to multiple PO and/or BO groups, the surfactants of the present invention may also contain varying amounts of EO groups to achieve the desired hydrophilic-lipophilic balance (HLB). The PO, BO and EO groups not only provide tolerance under harsh conditions, but they surprisingly also impart high surface activity, even without the large hydrophobe group previously thought necessary.

The PO and BO chains are very compatible with oil and somewhat compatible with water. The EO chain is very compatible with water and somewhat compatible with oil. Although the surfactants of the present invention lack a hard hydrophobe, it was surprisingly found the surfactants of the present invention performed similar to, or in some instances better than, conventional surfactants having a hard hydrophobe group.

The present invention is further directed to formulations comprising the surfactants of the invention, and methods of using the surfactants of the invention.

Definitions

Unless otherwise specified, the abbreviations and symbols used herein have their conventional meanings.

As used herein, the term "alkyl" embraces branched, cyclic or unbranched carbon chains, which may be fully saturated, mono- or polyunsaturated, and substituted or unsubstituted, having the designated number of carbon atoms. Examples of saturated alkyls included, but are not limited to, methyl, ethyl, n-propyl, isopropyl, n-butyl, isobutyl, t-butyl, sec-butyl, pentyl, hexyl, heptyl and octyl, and their isomers (e.g. iso or branched versions). The term "unsaturated alkyl" refers to alkyl groups having one or more double bonds or triple bonds.

As used herein, the term "alkoxy" embraces an alkyl group which has an oxygen atom attached thereto. Representative alkoxy groups include ethoxy, propoxy, isopropoxy, sec-propoxy, butoxy, iso-butoxy, sec-butoxy, tert-butoxy, and the like.

As used herein, the term "alcohol" embraces an alkyl group, which may be saturated or unsaturated, having one or more hydroxy (—OH) substituents. Primary and secondary alcohols are contemplated, such as mono-alcohols as well as polyhydroxy variants. Lower alcohols are those containing from about 1 to 4 carbon atoms. Exemplary alcohols include methanol, ethanol, 1-propanol, 2-propanol, 2-propen-1-ol, 1-butanol, 2-butanol, 2-methyl-2-propanol, 1-pentanol, 2-pentanol, 3-pentanol, and 3-methyl-1-butanol and their isomers.

As used herein, the term "polyamine" embraces organic groups having more than two amino groups and ending with two primary amino groups.

As used herein, the term "polyols" embraces polyhydric alcohols having 2 or more hydroxyl groups in both their monomeric and polymeric forms. Representative polyols include diols, such as ethylene glycol, propylene glycol, diethylene glycol, glycerol, pentaerythritol, di- and trihydroxymethyl alkanes, buanediols, 1-3 propanediols, alkyl glucosides (e.g. butyl), sorbitols, and polymers of the foregoing and other polyols, including polyglycerols, alkyl polyglucosides and polysaccharides, such as starches (e.g. CMC) and cycodextrins.

As used herein, the term "poloxamers" embraces nonionic triblock copolymers comprising a central PO chain flanked by two chains of EO, as well as the reverse arrangement, including those sold under the tradenames Pluronics, Synperonics and Kolliphor.

As used herein, the term "ionic" embraces cations, anions and ionic groups. For example, the term ionic would embrace both —$CO_2^-$ and —$CO_2H$.

As used herein, the term "zwitterionic" embraces groups having separate positively and negatively charged groups. Representative zwitterionic groups include betaines, sultaines, hydroxysultaines, sulfitobetaines, sulfatobetaines, phosphinate betaines, phosphonate betaines, phosphitobetaines, phosphatobetaines, and the like.

As used herein, the terms "include" and "including" are used in a non-limiting manner.

Compounds

In one aspect of the invention, surfactants of the present invention generally have the formula:

$$X-((A^1_x-A^2_y)-Y)_n \quad (I)$$

wherein X is an alcohol, an amine, or an alkyl- or alkoxy-amine having from 1 to 8 total carbons;

one of $A^1$ and $A^2$ is PO, butylene oxide (BO) and/or a combination of PO and BO, and the other of $A^1$ and $A^2$ is EO, and independent $A^1$ and $A^2$ groups may be in blocks and/or in random order;

x or y is 7-100 when $A^1$ or $A^2$, as applicable, is PO or BO;
x or y is 0-250 when $A^1$ or $A^2$, as applicable, is EO;
n is 1 to 4, or 1 to 3;
Y is an ionic group, a zwitterionic group or H; and
PO is —$CH_2CH(CH_3)$—O—, BO is —$CH_2CH(CH_2CH_3)$—O— or —$CH_2CH_2CH(CH_3)$—O— and EO is —$CH_2$—$CH_2$—O—.

The surfactants of the invention do not contain a traditional size hydrophobe. Instead, the total number of carbon atoms in the X group is from 1 to 8, but may be 1, 2, 3, 4, 5, 6, 7 or 8 or any range therebetween. For example, the X group may comprise 1-7, 1-6, 1-5, 1-4, 1-3 or 1-2 carbons.

In certain embodiments, $A^1$ and $A^2$ are preferably independently PO and EO, wherein $A^1$ and $A^2$ are not the same, and independent $A^1$ and $A^2$ groups may be in PO blocks, EO blocks, PO-EO blocks, EO-PO blocks, other repeating blocks and/or in random order. However, one or more PO groups, or all PO groups, may be replaced by BO. Preferably the surfactants of the present invention comprise a block of PO groups, followed by a block of EO groups.

In certain embodiments preferably, x or y is an integer from 7-100 when $A^1$ or $A^2$, as applicable, is PO, x or y is an integer from 0-250 when $A^1$ or $A^2$, as applicable, is EO, and at least one of the following is true: (x+y)≥25, or $R^1$=$C_1$-$C_6$.

In certain embodiments when $A^1$ or $A^2$ is PO and/or BO, x or y, as applicable, represents the total number of PO and BO groups and is an integer from 7-90, from 7-80, from 7-70, from 7-60, from 7-50, from 7-40, from 7-30, from 7-20, from 7-15, from 90-100, from 80-100, from 70-100, from 60-100, from 50-100, from 40-100, from 30-100, from 20-100, from 15-100, from 10-100, from 5-100, from 15-25, from 25-35, from 35-45, from 45-55, from 55-65, from 65-75, from 75-85, from 85-95, or any values or ranges therebetween.

In certain embodiments when $A^1$ or $A^2$ is EO, x or y, as applicable, is an integer from 0-250, from 0-230, from 0-210, from 0-190, from 0-170, from 0-150, from 0-130, from 0-110, from 0-90, from 0-70, from 0-50, from 0-30, from 0-15, from 230-250, from 210-250, from 190-250, from 170-250, from 150-250, from 130-250, from 110-250, from 90-250, from 70-250, from 50-250, from 30-250, from 15-250, from 10-250, from 5-250, 5-25, from 25-45, from 45-65, from 65-85, from 85-105, from 105-125, from 125-145, from 145-165, from 165-185, from 185-205, from 205-225, from 225-250.

In one aspect of the invention, alkoxy polyalkoxylate surfactants of the present invention have the formula:

$$R^1-O-(A^1_x-A^2_y)-Z \quad (II)$$

wherein $R^1$ is $C_1$ to $C_8$ alkyl; $A^1$, $A^2$, x, and y are as defined in formula (I); and Z is an ionic group or H.

In certain embodiments, $R^1=C_1$ to $C_8$, linear, cyclic or branched, saturated or unsaturated alkyl (e.g. allyl, alkenyl or alkynyl), optionally substituted with 1 primary or secondary —OH group. For example, $R^1$ may be selected from a methyl, ethyl, n-propyl, isopropyl, n-butyl, isobutyl, t-butyl, sec-butyl, pentyl, hexyl, heptyl and octyl and their isomers (e.g. iso or branched versions). In certain embodiments, $R^1$ may include $C_1$-$C_8$, $C_1$-$C_7$, $C_1$-$C_6$, $C_1$-$C_5$, $C_1$-$C_4$, $C_1$-$C_3$, $C_1$-$C_2$ or methyl. Exemplary $R^1$ groups include methanol, phenol, propanol dimer alcohol, methylpentyl, or ethylhexyl (EH).

In certain embodiments, $A^1$ and $A^2$ are preferably independently PO and EO, wherein $A^1$ and $A^2$ are not the same, and independent $A^1$ and $A^2$ groups may be in PO blocks, BO blocks, PO-EO blocks, EO-PO blocks, other repeating blocks and/or in random order. However, one or more PO groups, or all PO groups, may be replaced by BO. Preferably the alkoxy polyalkoxylate surfactants of the present invention comprise a block of PO groups, followed by a block of EO groups.

In certain embodiments preferably, x or y is an integer from 7-100 when $A^1$ or $A^2$, as applicable, is PO, x or y is an integer from 0-250 when $A^1$ or $A^2$, as applicable, is EO, and at least one of the following is true: (x+y)≥25, or $R^1=C_1$-$C_6$.

In certain embodiments when $A^1$ or $A^2$ is PO, x or y, as applicable, is an integer from 7-90, from 7-80, from 7-70, from 7-60, from 7-50, from 7-40, from 7-30, from 7-20, from 7-15, from 90-100, from 80-100, from 70-100, from 60-100, from 50-100, from 40-100, from 30-100, from 20-100, from 15-100, from 10-100, from 5-100, from 15-25, from 25-35, from 35-45, from 45-55, from 55-65, from 65-75, from 75-85, from 85-95, or any values or ranges therebetween.

In certain embodiments when $A^1$ or $A^2$ is EO, x or y, as applicable, is an integer from 0-250, from 0-230, from 0-210, from 0-190, from 0-170, from 0-150, from 0-130, from 0-110, from 0-90, from 0-70, from 0-50, from 0-30, from 0-15, from 230-250, from 210-250, from 190-250, from 170-250, from 150-250, from 130-250, from 110-250, from 90-250, from 70-250, from 50-250, from 30-250, from 15-250, from 10-250, from 5-250, 5-25, from 25-45, from 45-65, from 65-85, from 85-105, from 105-125, from 125-145, from 145-165, from 165-185, from 185-205, from 205-225, from 225-250.

Z is preferably selected from the group consisting of H, sulfate (e.g. $OSO_3^-M^+$), carboxylate (e.g. —$CH_2C(O)OH$, —$CH_2C(O)O^-M^+$, —$CH_2CH_2$—$CO_2H$ or —$CH_2CH_2$—$CO_2^-$ or $M^+$), and sulfonate (—$R^2SO_3H$ or —$R^2SO_3^-M^+$ wherein $R^2$ is a $C_1$-$C_3$ alkyl), optionally substituted with one hydroxyl group; wherein $M^+$ is a monovalent, divalent or trivalent cation. $M^+$ may be a metal cation, and in some embodiments is $NH_4^+$, $Na^+$ or $K^+$. It should be understood that the oxygen of the EO or PO group may contribute to the sulfate group, such that unless otherwise specified, as used herein, $R^1$—$PO_x$-$EO_y$—$SO_4H$ and $R^1$—O—$PO_x$-$EO_y$—$SO_3H$, for example, both refer to the sulfate. Above a certain level of PO groups without an EO group, a sulfate, carboxylate or sulfonate group needs to be present to give hydrophilicity to the surfactant. In certain embodiments, if there is no EO group, Z is not H. Preferably, if there are 5 or more, 7 or more or 21 or more PO groups without an EO group, Z is not H.

Certain exemplary alkoxy polyalkoxylate surfactants of the invention include those described above, in the examples, and the following:

$R^1$—O-7PO-xEO-Z; x: 0, 5, 10, 15, 20, 30, 45, 60, 75, 100, 120, 140, 160, 180, 200, 225, 250.

$R^1$—O-10PO-xEO-Z; x: 0, 5, 10, 15, 20, 30, 45, 60, 75, 100, 120, 140, 160, 180, 200, 225, 250.

$R^1$—O-21PO-xEO-Z; x: 0, 5, 10, 15, 20, 30, 45, 60, 75, 100, 120, 140, 160, 180, 200, 225, 250.

$R^1$—O-40PO-xEO-Z; x: 0, 5, 10, 15, 20, 30, 45, 60, 75, 100, 120, 140, 160, 180, 200, 225, 250.

$R^1$—O-45PO-xEO-Z; x: 0, 5, 10, 15, 20, 30, 45, 60, 75, 100, 120, 140, 160, 180, 200, 225, 250.

$R^1$—O-60PO-xEO-Z; x: 0, 5, 10, 15, 20, 30, 45, 60, 75, 100, 120, 140, 160, 180, 200, 225, 250.

$R^1$—O-70PO-xEO-Z; x: 0, 5, 10, 15, 20, 30, 45, 60, 75, 100, 120, 140, 160, 180, 200, 225, 250.

$R^1$—O-80PO-xEO-Z; x: 0, 5, 10, 15, 20, 30, 45, 60, 75, 100, 120, 140, 160, 180, 200, 225, 250.

$R^1$—O-100PO-xEO-Z; x: 0, 5, 10, 15, 20, 30, 45, 60, 75, 100, 120, 140, 160, 180, 200, 225, 250.

In each case, the PO and EO numbers may be the values listed, or the ranges defined by consecutive values. For example, 7-10PO, 10-21PO, etc., and 0-5EO, 5-10EO, etc. The order of the PO and EO groups may be reversed, or the PO and EO groups may be in random order, with the total number of groups as listed.

In one aspect of the invention, polyol alkoxylate surfactants of the invention have the formula:

$$R^1_a-CH_b-(CH_2-O-(A^1_x-A^2_y)-Z)_n \quad (III)$$

wherein a+b+n=4; a=0-3; b=0-3; n=1-4; $R^1$ is $C_1$ to $C_6$ alkyl; $A^1$, $A^2$, x, and y are as described above with respect to formula (I); and Z is an ionic group or H.

In certain embodiments, the total carbon atoms in a $R^1_a$—$CH_b$—($CH_2$—O—)n group is equal to or less than 8. $R^1=C_1$ to $C_6$, linear, cyclic or branched, saturated or unsaturated alkyl (e.g. allyl, alkenyl or alkynyl), optionally substituted with 1 primary or secondary —OH group. For example, $R^1$ may be selected from a methyl, ethyl, n-propyl, isopropyl, n-butyl, isobutyl, t-butyl, sec-butyl, pentyl, hexyl, and their isomers (e.g. iso or branched versions). $R^1$ may include $C_1$-$C_6$, $C_1$-$C_5$, $C_1$-$C_4$, $C_1$-$C_3$, $C_1$-$C_2$, or methyl or may not be present. For example, if only one $R^1$ group is present and n=1, $R^1$ is $C_1$-$C_6$; if n=2, $R^1$ is $C_1$-$C_5$; and if n=3; $R^1$ is $C_1$-$C_4$. Exemplary surfactants include $CH_3CH_2$—C—($CH_2$—O—$PO_x$-$EO_y$)$_3$ from trimethylol propane.

In certain embodiments, $A^1$ and $A^2$ are preferably independently PO and EO, wherein $A^1$ and $A^2$ are not the same, and independent $A^1$ and $A^2$ groups may be in PO blocks, BO blocks, PO-EO blocks, EO-PO blocks, other repeating blocks and/or in random order. However, one or more PO groups, or all PO groups, may be replaced by BO. Preferably the alkoxy polyalkoxylate surfactants of the present invention comprise a block of PO groups, followed by a block of EO groups.

In certain embodiments preferably, x or y is an integer from 7-100 when $A^1$ or $A^2$, as applicable, is PO, x or y is an integer from 0-250 when $A^1$ or $A^2$, as applicable, is EO, and at least one of the following is true: (x+y)≥25, or $R^1=C_1-C_6$.

In certain embodiments when $A^1$ or $A^2$ is PO, x or y, as applicable, is an integer from 7-90, from 7-80, from 7-70, from 7-60, from 7-50, from 7-40, from 7-30, from 7-20, from 7-15, from 90-100, from 80-100, from 70-100, from 60-100, from 50-100, from 40-100, from 30-100, from 20-100, from 15-100, from 10-100, from 5-100, from 15-25, from 25-35, from 35-45, from 45-55, from 55-65, from 65-75, from 75-85, from 85-95, or any values or ranges therebetween.

In certain embodiments when $A^1$ or $A^2$ is EO, x or y, as applicable, is an integer from 0-250, from 0-230, from 0-210, from 0-190, from 0-170, from 0-150, from 0-130, from 0-110, from 0-90, from 0-70, from 0-50, from 0-30, from 0-15, from 230-250, from 210-250, from 190-250, from 170-250, from 150-250, from 130-250, from 110-250, from 90-250, from 70-250, from 50-250, from 30-250, from 15-250, from 10-250, from 5-250, 5-25, from 25-45, from 45-65, from 65-85, from 85-105, from 105-125, from 125-145, from 145-165, from 165-185, from 185-205, from 205-225, from 225-250.

Z is preferably selected from the group consisting of H, sulfate (e.g. $OSO_3^- M^+$), carboxylate (e.g. $—CH_2C(O)OH$, $—CH_2C(O)O^-M^+$, $—CH_2CH_2—CO_2H$ or $—CH_2CH_2—CO_2^-$ or $M^+$), and sulfonate ($—R^2SO_3H$ or $—R^2SO_3^-M^+$ wherein $R^2$ is a $C_1-C_3$ alkyl), optionally substituted with one hydroxyl group; wherein $M^+$ is a monovalent, divalent or trivalent cation. $M^+$ may be a metal cation, and in some embodiments is $NH_4^+$, $Na^+$ or $K^+$. In certain embodiments, if there is no EO group, Z is not H. Preferably, if there are 5 or more, 7 or more or 21 or more PO groups without an EO group, Z is not H.

Certain exemplary alkoxy polyalkoxylate surfactants of the invention include those described above, in the examples, and the following:

$R^1_a$—$CH_b$—$(CH_2$—O-7PO-xEO-Z)n; x: 0, 5, 10, 15, 20, 30, 45, 60, 75, 100, 120, 140, 160, 180, 200, 225, 250.

$R^1_a$—$CH_b$—$(CH_2$—O-10PO-xEO-Z)n; x: 0, 5, 10, 15, 20, 30, 45, 60, 75, 100, 120, 140, 160, 180, 200, 225, 250.

$R^1_a$—$CH_b$—$(CH_2$—O-21PO-xEO-Z)n; x: 0, 5, 10, 15, 20, 30, 45, 60, 75, 100, 120, 140, 160, 180, 200, 225, 250.

$R^1_a$—$CH_b$—$(CH_2$—O-40PO-xEO-Z)n; x: 0, 5, 10, 15, 20, 30, 45, 60, 75, 100, 120, 140, 160, 180, 200, 225, 250.

$R^1_a$—$CH_b$—$(CH_2$—O-45PO-xEO-Z)n; x: 0, 5, 10, 15, 20, 30, 45, 60, 75, 100, 120, 140, 160, 180, 200, 225, 250.

$R^1_a$—$CH_b$—$(CH_2$—O-60PO-xEO-Z)n; x: 0, 5, 10, 15, 20, 30, 45, 60, 75, 100, 120, 140, 160, 180, 200, 225, 250.

$R^1_a$—$CH_b$—$(CH_2$—O-70PO-xEO-Z)n; x: 0, 5, 10, 15, 20, 30, 45, 60, 75, 100, 120, 140, 160, 180, 200, 225, 250.

$R^1_a$—$CH_b$—$(CH_2$—O-80PO-xEO-Z)n; x: 0, 5, 10, 15, 20, 30, 45, 60, 75, 100, 120, 140, 160, 180, 200, 225, 250.

$R^1_a$—$CH_b$—$(CH_2$—O-100PO-xEO-Z)n; x: 0, 5, 10, 15, 20, 30, 45, 60, 75, 100, 120, 140, 160, 180, 200, 225, 250.

In each case, the PO and EO numbers may be the values listed, or the ranges defined by consecutive values. For example, 7-10PO, 10-21PO, etc., and 0-5EO, 5-10EO, etc. The order of the PO and EO groups may be reversed, or the PO and EO groups may be in random order, with the total number of groups as listed.

In one aspect of the invention, polyol alkoxylate surfactants of the invention have the following formula:

polyol-$((A^1_x-A^2_y)Z)_n$  (IV)

wherein one or more of the hydrogen molecules of one or more hydroxyl groups of the polyol is replaced with $(A^1_x-A^2_y)Z$; $A^1$, $A_2$, x, and y are as described above with respect to formula (I); Z is an ionic group or H; and n is equal to or less than the total number of hydroxyl groups on the polyol, such that not all of the hydroxyl groups are alkoxylated. For example, polypropylene glycol may be mono or difunctionalized with $(A^1_x-A^2_y)Z$, wherein n=1 or 2.

Suitable polyols include monomeric or polymeric polyols, including diols, such as ethylene glycol, propylene glycol, diethylene glycol, glycerol, pentaerythritol, di- and trihydroxymethyl alkanes, buanediols, 1-3 propanediols, alkyl glucosides (e.g. butyl), sorbitols, and polymers of the foregoing and other polyols, including polyglycerols, alkyl polyglucosides and polysaccharides, such as starches (e.g. CMC) and cyclodextrins, and poloxamers (e.g. Pluronics and reverse Pluronics), in each case preferably comprising $C_1$ to $C_5$ linear, cyclic (e.g. phenyl) or branched alkyl groups. For the polyol polyalkoxylate surfactants, although the alkyl groups will preferably have 5 or fewer carbons, the total number of carbons in the polyol may be greater than 8.

In certain embodiments, $A^1$ and $A^2$ are preferably independently PO and EO, wherein $A^1$ and $A^2$ are not the same, and independent $A^1$ and $A^2$ groups may be in PO blocks, BO blocks, PO-EO blocks, EO-PO blocks, other repeating blocks and/or in random order. However, one or more PO groups, or all PO groups, may be replaced by BO. Preferably the alkoxy polyalkoxylate surfactants of the present invention comprise a block of PO groups, followed by a block of EO groups.

In certain embodiments preferably, x or y is an integer from 7-100 when $A^1$ or $A^2$, as applicable, is PO, x or y is an integer from 0-250 when $A^1$ or $A^2$, as applicable, is EO.

In certain embodiments when $A^1$ or $A^2$ is PO, x or y, as applicable, is an integer from 7-90, from 7-80, from 7-70, from 7-60, from 7-50, from 7-40, from 7-30, from 7-20, from 7-15, from 90-100, from 80-100, from 70-100, from 60-100, from 50-100, from 40-100, from 30-100, from 20-100, from 15-100, from 10-100, from 5-100, from 15-25, from 25-35, from 35-45, from 45-55, from 55-65, from 65-75, from 75-85, from 85-95, or any values or ranges therebetween.

In certain embodiments when $A^1$ or $A^2$ is EO, x or y, as applicable, is an integer from 0-250, from 0-230, from 0-210, from 0-190, from 0-170, from 0-150, from 0-130, from 0-110, from 0-90, from 0-70, from 0-50, from 0-30, from 0-15, from 230-250, from 210-250, from 190-250, from 170-250, from 150-250, from 130-250, from 110-250, from 90-250, from 70-250, from 50-250, from 30-250, from 15-250, from 10-250, from 5-250, 5-25, from 25-45, from 45-65, from 65-85, from 85-105, from 105-125, from 125-145, from 145-165, from 165-185, from 185-205, from 205-225, from 225-250.

Z is preferably selected from the group consisting of H, sulfate (e.g. $OSO_3^-M^+$), carboxylate (e.g. $—CH_2C(O)OH$, $—CH_2C(O)O^-M^+$, $—CH_2CH_2—CO_2H$ or $—CH_2CH_2—CO_2^-$ or $M^+$), and sulfonate ($—R^2SO_3H$ or $—R^2SO_3^-M^+$ wherein $R^2$ is a $C_1-C_3$ alkyl), optionally substituted with one hydroxyl group; wherein $M^+$ is a monovalent, divalent or trivalent cation. $M^+$ may be a metal cation, and in some embodiments is $NH_4^+$, $Na^+$ or $K^+$. In certain embodiments, if there is no EO group, Z is not H. Preferably, if there are 5 or more, 7 or more or 21 or more PO groups without an EO group, Z is not H.

Certain exemplary polyol polyalkoxylate surfactants of the invention include those described above, in the examples, and the following:

Polyol-(7PO-xEO-Z)n; x: 0, 5, 10, 15, 20, 30, 45, 60, 75, 100, 120, 140, 160, 180, 200, 225, 250.

Polyol-(10PO-xEO-Z)n; x: 0, 5, 10, 15, 20, 30, 45, 60, 75, 100, 120, 140, 160, 180, 200, 225, 250.

Polyol-(21PO-xEO-Z)n; x: 0, 5, 10, 15, 20, 30, 45, 60, 75, 100, 120, 140, 160, 180, 200, 225, 250.

Polyol-(40PO-xEO-Z)n; x: 0, 5, 10, 15, 20, 30, 45, 60, 75, 100, 120, 140, 160, 180, 200, 225, 250.

Polyol-(45PO-xEO-Z)n; x: 0, 5, 10, 15, 20, 30, 45, 60, 75, 100, 120, 140, 160, 180, 200, 225, 250.

Polyol-(60PO-xEO-Z)n; x: 0, 5, 10, 15, 20, 30, 45, 60, 75, 100, 120, 140, 160, 180, 200, 225, 250.

Polyol-(70PO-xEO-Z)n; x: 0, 5, 10, 15, 20, 30, 45, 60, 75, 100, 120, 140, 160, 180, 200, 225, 250.

Polyol-(80PO-xEO-Z)n; x: 0, 5, 10, 15, 20, 30, 45, 60, 75, 100, 120, 140, 160, 180, 200, 225, 250.

Polyol-(100PO-xEO-Z)n; x: 0, 5, 10, 15, 20, 30, 45, 60, 75, 100, 120, 140, 160, 180, 200, 225, 250.

In each case, the PO and EO numbers may be the values listed, or the ranges defined by consecutive values. For example, 7-10PO, 10-21PO, etc., and 0-5EO, 5-10EO, etc. The order of the PO and EO groups may be reversed, or the PO and EO groups may be in random order, with the total number of groups as listed.

In one aspect of the invention, amine, alkoxyamine and alkylamine polyalkoxylate surfactants of the invention have the formula:

$$R^1_a\text{---}NH_m((R^3O)_d(A^1_x\text{-}A^2_y)Y)_n \quad (V)$$

wherein $a+m+n=3$; $a=0$-$2$; $m=0$-$2$; $d=0$-$1$; $n=1$-$3$; $R^3$ and $R^1$ are independently $C_1$ to $C_8$ alkyl, with a combined total of 8 or fewer carbons; $A^1$, $A^2$, x, and y are as described above with respect to formula (I); and Y is H, an ionic group, a zwitterionic group, or a cationic when the nitrogen atom is quaternary, with a positive charge, and a negatively charged anion as a counterion.

In certain such embodiments, $R^1$ and $R^3$ are independently=$C_1$ to $C_8$, linear, cyclic or branched, saturated or unsaturated alkyl (e.g. allyl, alkenyl or alkynyl), optionally substituted with 1 primary or secondary —OH group. For example, $R^1$ and $R^3$ may be selected from a methyl, ethyl, n-propyl, isopropyl, n-butyl, isobutyl, t-butyl, sec-butyl, pentyl, hexyl, heptyl and octyl and their isomers (e.g. iso or branched versions), provided the total number of carbons does not exceed 8. $R^1$ and $R^3$ may independently include $C_1$-$C_8$, $C_1$-$C_6$, $C_1$-$C_5$, $C_1$-$C_4$, $C_1$-$C_3$, $C_1$-$C_2$, or methyl, or either or both of $R^1$ and $R^3$ may not be present. In exemplary embodiments, when $d=1$, $R^3$ is $C_1$-$C_3$ alkyl, or $C_1$-$C_2$ alkyl. Exemplary surfactants include N—(CH$_2$CH$_2$O—(POxEOy)Y)$_3$.

In certain embodiments, $A^1$ and $A^2$ are preferably independently PO and EO, wherein $A^1$ and $A^2$ are not the same, and independent $A^1$ and $A^2$ groups may be in PO blocks, BO blocks, PO-EO blocks, EO-PO blocks, other repeating blocks and/or in random order. However, one or more PO groups, or all PO groups, may be replaced by BO. Preferably, the alkoxy polyalkoxylate surfactants of the present invention comprise a block of PO groups, followed by a block of EO groups.

In certain embodiments preferably, x or y is an integer from 7-100 when $A^1$ or $A^2$, as applicable, is PO, x or y is an integer from 0-250 when $A^1$ or $A^2$, as applicable, is EO, and at least one of the following is true: $(x+y) \geq 25$, or $R^1=C_1$-$C_6$.

In certain embodiments when $A^1$ or $A^2$ is PO, x or y, as applicable, is an integer from 7-90, from 7-80, from 7-70, from 7-60, from 7-50, from 7-40, from 7-30, from 7-20, from 7-15, from 90-100, from 80-100, from 70-100, from 60-100, from 50-100, from 40-100, from 30-100, from 20-100, from 15-100, from 10-100, from 5-100, from 15-25, from 25-35, from 35-45, from 45-55, from 55-65, from 65-75, from 75-85, from 85-95, or any values or ranges therebetween.

In certain embodiments when $A^1$ or $A^2$ is EO, x or y, as applicable, is an integer from 0-250, from 0-230, from 0-210, from 0-190, from 0-170, from 0-150, from 0-130, from 0-110, from 0-90, from 0-70, from 0-50, from 0-30, from 0-15, from 230-250, from 210-250, from 190-250, from 170-250, from 150-250, from 130-250, from 110-250, from 90-250, from 70-250, from 50-250, from 30-250, from 15-250, from 10-250, from 5-250, 5-25, from 25-45, from 45-65, from 65-85, from 85-105, from 105-125, from 125-145, from 145-165, from 165-185, from 185-205, from 205-225, from 225-250.

Amine, alkoxyamine and alkylamine polyalkoxylate surfactants of the present invention can behave as switchable surfactants, depending on the pH of the formulation, as well as betaines. Y is preferably selected from the group consisting of H, a zwitterionic group and a cationic when the nitrogen atom is quaternary, with a positive charge, and a negatively charged anion as a counterion. Suitable zwitterionic groups include betaines (e.g. $CH_2CO_2^-$), sultaines (e.g. $(CH_2)_dSO_3^-$, wherein $d=1$-$3$), and hydroxysultaines (e.g. $CH_2CHOHCH_2SO_3^-$).

Certain exemplary amine, alkoxyamine and alkylamine polyalkoxylate surfactants of the invention include those described above, in the examples, and the following:

N—((POx-EOy)Y)$_3$
$R^1$N((POx-EOy)Y)$_2$
$(R^1)_2$N(POx-EOy)Y
N—(R$^3$—O—(POxEOx)Y)$_3$
$R^1$N((R$^3$—O—POx-EOy)Y)$_2$
$(R^1)_2$N(R$^3$—O—POx-EOy)Y in each case wherein PO and EO may be as follows:

(7PO-xEO-Y); x: 0, 5, 10, 15, 20, 30, 45, 60, 75, 100, 120, 140, 160, 180, 200, 225, 250.

(10PO-xEO-Y); x: 0, 5, 10, 15, 20, 30, 45, 60, 75, 100, 120, 140, 160, 180, 200, 225, 250.

(21PO-xEO-Y); x: 0, 5, 10, 15, 20, 30, 45, 60, 75, 100, 120, 140, 160, 180, 200, 225, 250.

(40PO-xEO-Y); x: 0, 5, 10, 15, 20, 30, 45, 60, 75, 100, 120, 140, 160, 180, 200, 225, 250.

(45PO-xEO-Y); x: 0, 5, 10, 15, 20, 30, 45, 60, 75, 100, 120, 140, 160, 180, 200, 225, 250.

(60PO-xEO-Y); x: 0, 5, 10, 15, 20, 30, 45, 60, 75, 100, 120, 140, 160, 180, 200, 225, 250.

(70PO-xEO-Y); x: 0, 5, 10, 15, 20, 30, 45, 60, 75, 100, 120, 140, 160, 180, 200, 225, 250.

(80PO-xEO-Y); x: 0, 5, 10, 15, 20, 30, 45, 60, 75, 100, 120, 140, 160, 180, 200, 225, 250.

(100PO-xEO-Y); x: 0, 5, 10, 15, 20, 30, 45, 60, 75, 100, 120, 140, 160, 180, 200, 225, 250.

In each case, the PO and EO numbers may be the values listed, or the ranges defined by consecutive values. For example, 7-10PO, 10-21PO, etc., and 0-5EO, 5-10EO, etc. The order of the PO and EO groups may be reversed, or the PO and EO groups may be in random order, with the total number of groups as listed.

In one aspect of the invention, polyamine polyalkoxylate surfactants of the invention have the formula:

$$\text{polyamine-}((A^1_x\text{-}A^2_y)Y)_n \quad (VI)$$

wherein one or more polyalkoxy groups $(A^1_x\text{-}A^2_y)Y$ are attached to one or more of the nitrogen atoms of the polyamine, and $A^1$, $A^2$, x, and y are as described above with respect to formula (I); Y is H, an ionic group, a zwitterionic group, or a cationic when the nitrogen atom is quaternary, with a positive charge, and a negatively charged anion as a counterion; and n is equal to or less than the number of displaceable hydrogens on the nitrogen atoms. For example, when the polyamine is triethylene tetramine (TETA): $NH_2CH_2CH_2NHCH_2CH_2NHCH_2CH_2NH_2$, one or more of the hydrogen atoms attached to one or more of the nitrogen atoms may be replaced with $(A^1_x\text{-}A^2_y)Y$.

Preferably the polyamine comprise up to 9 nitrogen atoms and up to 8 carbon atoms. The polyamine may comprise 1, 2, 3, 4, 5, 6, 7 or 8 carbon atoms, or any range therebetween. For example, the polyamine group may comprise 1-7, 1-6, 1-5, 1-4, 1-3 or 1-2 carbons.

Polyamine polyalkoxylate surfactants of the present invention can behave as switchable surfactants, depending on the pH of the formulation, as well as betaines. Y is preferably selected from the group consisting of H, a zwitterionic group and a cationic when the nitrogen atom is quaternary, with a positive charge, and a negatively charged anion as a counterion. Suitable zwitterionic groups include betaines, sultaines, and hydroxysultaines.

In certain embodiments, $A^1$ and $A^2$ are preferably independently PO and EO, wherein $A^1$ and $A^2$ are not the same, and independent $A^1$ and $A^2$ groups may be in PO blocks, BO blocks, PO-EO blocks, EO-PO blocks, other repeating blocks and/or in random order. However, one or more PO groups, or all PO groups, may be replaced by BO. Preferably the alkoxy polyalkoxylate surfactants of the present invention comprise a block of PO groups, followed by a block of EO groups.

In certain embodiments preferably, x or y is an integer from 7-100 when $A^1$ or $A^2$, as applicable, is PO, x or y is an integer from 0-250 when $A^1$ or $A^2$, as applicable, is EO.

In certain embodiments when $A^1$ or $A^2$ is PO, x or y, as applicable, is an integer from 7-90, from 7-80, from 7-70, from 7-60, from 7-50, from 7-40, from 7-30, from 7-20, from 7-15, from 90-100, from 80-100, from 70-100, from 60-100, from 50-100, from 40-100, from 30-100, from 20-100, from 15-100, from 10-100, from 5-100, from 15-25, from 25-35, from 35-45, from 45-55, from 55-65, from 65-75, from 75-85, from 85-95, or any values or ranges therebetween.

In certain embodiments when $A^1$ or $A^2$ is EO, x or y, as applicable, is an integer from 0-250, from 0-230, from 0-210, from 0-190, from 0-170, from 0-150, from 0-130, from 0-110, from 0-90, from 0-70, from 0-50, from 0-30, from 0-15, from 230-250, from 210-250, from 190-250, from 170-250, from 150-250, from 130-250, from 110-250, from 90-250, from 70-250, from 50-250, from 30-250, from 15-250, from 10-250, from 5-250, 5-25, from 25-45, from 45-65, from 65-85, from 85-105, from 105-125, from 125-145, from 145-165, from 165-185, from 185-205, from 205-225, from 225-250.

Certain exemplary polyamine polyalkoxylate surfactants of the invention include those described above, in the examples, and the following:

Polyamine-(7PO-xEO-Y)n; x: 0, 5, 10, 15, 20, 30, 45, 60, 75, 100, 120, 140, 160, 180, 200, 225, 250.
Polyamine-(10PO-xEO-Y)n; x: 0, 5, 10, 15, 20, 30, 45, 60, 75, 100, 120, 140, 160, 180, 200, 225, 250.
Polyamine-(21PO-xEO-Y)n; x: 0, 5, 10, 15, 20, 30, 45, 60, 75, 100, 120, 140, 160, 180, 200, 225, 250.
Polyamine-(40PO-xEO-Y)n; x: 0, 5, 10, 15, 20, 30, 45, 60, 75, 100, 120, 140, 160, 180, 200, 225, 250.
Polyamine-(45PO-xEO-Y)n; x: 0, 5, 10, 15, 20, 30, 45, 60, 75, 100, 120, 140, 160, 180, 200, 225, 250.
Polyamine-(60PO-xEO-Y)n; x: 0, 5, 10, 15, 20, 30, 45, 60, 75, 100, 120, 140, 160, 180, 200, 225, 250.
Polyamine-(70PO-xEO-Y)n; x: 0, 5, 10, 15, 20, 30, 45, 60, 75, 100, 120, 140, 160, 180, 200, 225, 250.
Polyamine-(80PO-xEO-Y)n; x: 0, 5, 10, 15, 20, 30, 45, 60, 75, 100, 120, 140, 160, 180, 200, 225, 250.
Polyamine-(100PO-xEO-Y)n; x: 0, 5, 10, 15, 20, 30, 45, 60, 75, 100, 120, 140, 160, 180, 200, 225, 250.

In each case, the PO and EO numbers may be the values listed, or the ranges defined by consecutive values. For example, 7-10PO, 10-21PO, etc., and 0-5EO, 5-10EO, etc. The order of the PO and EO groups may be reversed, or the PO and EO groups may be in random order, with the total number of groups as listed.

The surfactants of the present invention, for example the compounds of formula (I), (II), (III), (IV), (V) and (VI), have advantages over conventional surfactants. For example, because they do not require use of high cost long carbon chain alcohols as a raw material, much cheaper and versatile alcohols, such as methanol, phenol, and 2ethylhexanol, can be used. Due to the lower hydrophobicity of PO groups at room conditions, they form clear aqueous solutions at such conditions, which can be injected into oil reservoirs in EOR applications. This can be particularly helpful for high-temperature/high-salinity reservoirs. In addition, the surfactants of the present invention are likely to have lower adsorption on the rock since they do not have a hard (large) hydrophobe.

It was surprisingly found indications that use of short hydrophobe surfactants demonstrated preferential interaction with lower hydrocarbons. This allows the surfactants of the present invention to address components of the oil that were not able to be addressed by conventional hydrophobe surfactants. It may be that there could be a certain correlation between the carbon chain length of the surfactant and the hydrocarbon chain length, such that smaller carbon chain length surfactants can be used to address lower hydrocarbons in the oil, and longer carbon chain length surfactants can be used to address higher hydrocarbons in the oil. This would enable a surfactant blend, comprising surfactants of the invention and conventional surfactants, to be developed to address the specific hydrocarbon makeup of a target oil fraction.

As described in more detail in the examples, the surfactants of the present invention were found to have very low CMC values, and lowered the surface tension to about 32 dynes/cm, similar to conventional surfactants such as $C_{12\text{-}13}$-7PO-sulfate, $C_{20\text{-}24}$ IOS and $C_{15\text{-}18}$ IOS. This shows that these surfactant molecules were surface active even though they did not have a hard hydrophobe. The CMC values of the novel surfactants were much lower than that of conventional surfactants.

The aqueous stability (solubility) of the surfactants of the present invention at a given temperature was found to be dependent on the number of PO and EO groups. As EO increases, aqueous stability increases without affecting the oil-brine-surfactant phase behavior. The surfactants of the present invention showed higher hydrophobicity at higher temperatures. Aqueous stability improved with co-surfactants. The aqueous stability results are comparable with conventional surfactants.

Phase behavior experiments of the surfactants of the present invention showed low IFT formulations with different crude oils at 40° C. and 60° C. by using these surfactants by themselves and ultralow IFT when used as in combination with internal olefin sulfonates (IOS). The solubilization ratios around their respective optimum salinities were in the range of 9-12 cc/cc. Most formulations tested were aqueous stable at their respective optimum salinities. The optimum salinities (and the respective solubilization ratios) of the surfactants of the invention were similar to that of the conventional surfactants tested. In some cases, the solubilization ratios (at the optimum salinity) were higher with the conventional surfactants due to the presence of a hard hydrophobe. As needed, the surfactants of the present invention can be used in conjunction with hard hydrophobe surfactants to maximize the efficiencies.

Satisfactory oil recoveries and low surfactant retention were obtained in coreflood experiments using the surfactants of the present invention. The surfactants showed enhanced foam stability in the presence of crude oil under high salinity/high temperature conditions. The surfactants further showed viscoelastic behavior at temperatures ranging from 25° C. to 100° C. The viscoelastic behavior was maintained in the presence of small amounts (5-10%) of crude oils and alkanes.

Formulations

The present invention is directed to formulations comprising one or more surfactants of the present invention, which may be selected from any of the surfactant compounds described herein, for example a compound of formula (I), (II), (III), (IV), (V) or (VI). The formulations of the invention may comprise the surfactant of the present invention either alone or in combination with other compounds.

Preferably the formulations of the present invention are aqueous compositions comprising a surfactant of the invention, for example a compound of formula (I), (II), (III), (IV), (V) or (VI). Formulations of the present invention also include emulsions, wherein a surfactant of the present invention, for example a compound of formula (I), (II), (III), (IV), (V) or (VI), is present in the aqueous phase, and the other phase may be a hydrocarbon phase, such as an unrefined petroleum phase.

In certain embodiments, the formulations of the present invention comprise the surfactants of the present in invention, for example a compound of formula (I), (II), (III), (IV), (V) or (VI), and one or more co-surfactants. Suitable co-surfactants may include conventional surfactants for the intended use of the formulation, for example detergent-type surfactants. Suitable co-surfactants may be anionic, non-ionic, zwitterionic or cationic surfactants. In some embodiments, the co-surfactant comprises one or more of an alfa olefin sulfonate (AOS), an internal olefin sulfonate (IOS), triethylene glycol mono butyl ester (TEGBE), an alkyl aryl sulfonate (ARS), an alkyl benzene sulfonate (ABS), an alkane sulfonate, a petroleum sulfonate, an alkyl diphenyl oxide (di)sulfonate, an alcohol sulfate, an alkoxy sulfate, an alkoxy sulfonate, an alcohol phosphate, an alkoxy phosphate, a sulfosuccinate ester, an alcohol ethoxylate, an alkyl phenol ethoxylate, a quaternary ammonium salt, a betaine or a sultaine (including hydroxysultaines). Other useful co-surfactants are well-known in the art.

In certain embodiments, formulations of the present invention comprise the surfactants of the present invention, for example a compound of formula (I), (II), (III), (IV), (V) or (VI), are present with a co-surfactant in amounts sufficient to produce synergistic benefits over the surfactant and co-surfactant alone with respect to surface activity (e.g. interfacial tension lowering effect and/or surface tension lowering effect), stability, and/or solubility. The surfactants of the present invention have demonstrated good synergy with various co-surfactants and enhanced solubility at higher temperatures. The total surfactant concentration is preferably from 0.25 to 2.0 wt %, and may be from 0.25 to 0.5 wt %, 0.25 to 1.0 wt %, 0.25 to 1.5 wt %, 0.5% to 1%, 0.5 to 1.5%, or 0.5% to 2 wt % all values and ranges therebetween.

In certain embodiments, formulations of the present invention comprise one or more surfactants of the present invention, for example a compound of formula (I), (II), (III), (IV), (V) or (VI), and an alkali agent. Suitable alkali agents comprise basic, ionic salts of alkali metals (e.g. lithium, sodium, potassium) or alkaline earth metals (e.g. magnesium, calcium, barium, radium).

In certain embodiments, formulations of the present invention comprise a surfactant of the present invention, for example a compound of formula (I), (II), (III), (IV), (V) or (VI), and a polymer. Polymers may be employed as viscosity enhancers and/or mobility control agents. Suitable polymers include acrylamide polymers or co-polymers, and bio-polymers, such as those based on polysaccharides (e.g. xanthan gum) or hydroxyalkyl cellulose. Where polymers cannot be employed for mobility control, stable foam may be employed as an alternative.

In certain embodiments, formulations of the present invention comprise a surfactant of the present invention, for example a compound of formula (I), (II), (III), (IV), (V) or (VI), and a co-solvent. Suitable co-solvents include alcohols, alcohol ethoxylates, glycol ethers, glycols and glycerol.

In certain embodiments, formulations of the present invention comprise a surfactant of the present invention, for example a compound of formula (I), (II), (III), (IV), (V) or (VI), and a gas, a pH modifier and/or a salinity enhancing agent.

It should be understood that the formulations of the present invention may comprise a surfactant of the present invention, for example a compound of formula (I), (II), (III), (IV), (V) or (VI), and combinations of one or more of the co-surfactants, polymers, co-solvents, alkali agents, gasses, pH modifiers and salinity enhancing agents discussed above in any combination, in an aqueous composition or the aqueous phase of an emulsion. For example, a formulation of the present invention may comprise a surfactant of the present invention with a co-surfactant but without a co-solvent.

In certain embodiments, formulations of the present invention comprising a surfactant of the present invention, for example a compound of formula (I), (II), (III), (IV), (V) or (VI), have a pH of 4 to 10, including a pH of 4, 5, 6, 7, 8, 9, or 10 and all values and ranges therebetween. Formulations of the amine based surfactants of the present invention could be buffered to a pH of 10 or less for hard brine environments to prevent divalent ion precipitation as hydroxides. In soft brine, the pH greater than 11 of the amine functionality can be used advantageously in alkaline formulations.

Uses

In certain embodiments, the surfactants of the present invention, for example a compound of formula (I), (II), (III), (IV), (V) or (VI), are used in enhanced oil recovery (EOR) applications. Such EOR applications may include surfactant flooding, e.g. alkali surfactant polymer (ASP) floods, alkali co-solvent polymer (ACP) floods, surfactant polymer (SP) floods, and low salinity floods, steam assisted gravity drainage (SAGD), wettability alteration, enhanced imbibition, foam floods, hot water injection, and injectivity enhancement.

The surfactants of the present invention may be suitable for use, in a wide variety of rock environments, including in shale applications. Further, because surfactants of the invention do not contain a 'hard' hydrophobe, they are therefore likely to show lower retention in the porous media during oil recovery floods.

The formulations of the surfactants of the present invention, for example a compound of formula (I), (II), (III), (IV), (V) or (VI), having high viscosity, such as those comprising betaines and hydroxysultaines, can be used in EOR applications in areas with very low permeability. Such areas do not allow the use of high viscosity polymers, which are too large to pass through the pores. However, the combined high viscosity and small size of certain surfactants of the present invention allow the formulation to be pushed through the pores.

In certain aspects of the invention, the surfactants of the present invention are used to displace a hydrocarbon material, such as unrefined petroleum, that is in contact with a solid material, such as a rock. The process includes contacting the hydrocarbon material with a compound of the present invention, for example a compound of formula (I), (II), (III), (IV), (V) or (VI), when the hydrocarbon material is in contact with the solid material. The hydrocarbon material is allowed to separate from the solid material, which displaces the hydrocarbon material in contact with the solid material. The solid material may also be contacted with the compound of the present invention.

The surfactants of the present invention, for example a compound of formula (I), (II), (III), (IV), (V) or (VI), have oil field uses applicable both within and outside the field of EOR. For example, the surfactants of the present invention may be used as emulsion breakers, foam application (including using $CO_2$ as gas) for switchable surfactants, and water-in-gas (including $CO_2$) emulsions. The surfactants of the present invention may also be used in emulsion polymerization, as polymerizable surfactants. For example, the unsaturated surfactants of the present invention can be used to make homo or co-polymers.

The surfactants of the present invention, for example a compound of formula (I), (II), (III), (IV), (V) or (VI), can be used in combination with, in part replacement of or in place of, most conventional surfactants. For example, the surfactants of the present invention can be used for various detergency and cleaning applications, which may include, cleaning of crude oil storage tanks, and household, institutional and industrial cleaning, such as foaming, hard surface cleaning, and hard water applications. The surfactants of the present invention may also be used in emulsions for organic chemicals for agricultural applications, paper deinking, organic and inorganic pigment dispersion, and textile and leather processing.

Certain aspects of the invention are illustrated in the following non-limiting examples.

Materials: The materials used in the examples consisted of surfactants, polymers, and common salts. The novel surfactants were synthesized by Harcros Chemicals (Kansas, USA). Evaluation work was performed at The University of Texas. The IOS surfactants were obtained from Shell chemicals. The polymers were obtained in powdered form from SNF (Cedex, France). Common salts such as sodium chloride, calcium chloride and magnesium chloride were obtained from Thermo Fisher Scientific. The borosilicate tubes used in surfactant phase behavior studies were also obtained from Thermo Fisher Scientific. The outcrop sandstone cores used in the oil recovery corefloods were obtained from Kocurek Industries (Caldwell, Tex.). The crude oil used in the corefloods had the viscosity of about 4 cP at 40° C. and 2.7 cP at 65° C.

Example 1

Surface Tension

Surface tension (ST) values of surfactant solutions as a function of surfactant concentrations were measured at room conditions using the pendant drop method. Rame-Hart goniometer instrument was used for this purpose. The measured ST values were plotted against the corresponding surfactant concentrations. The minimum surfactant concentration above which no reduction (or slight reduction) in ST is observed is reported as the CMC.

Figure 2:
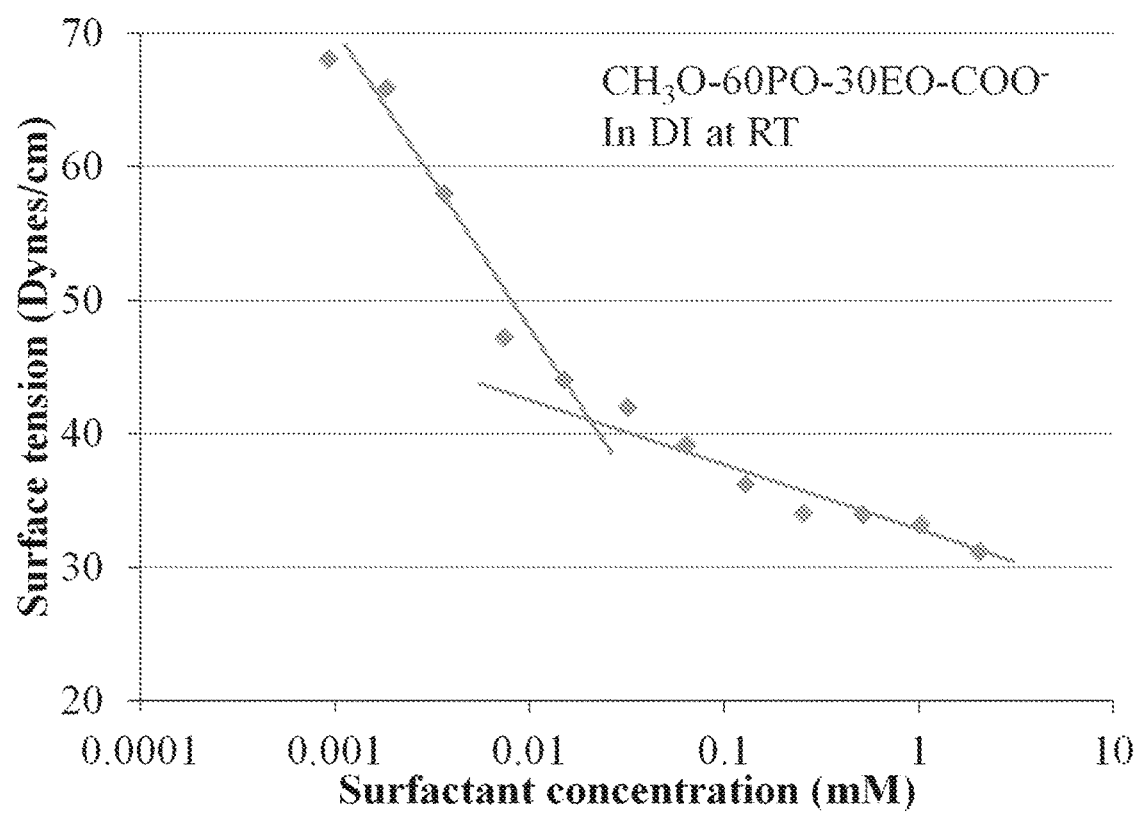
FIG. 2 depicts surface tension measurements of $CH_3O$-60PO-30EO-carboxylate.
Figure 3:
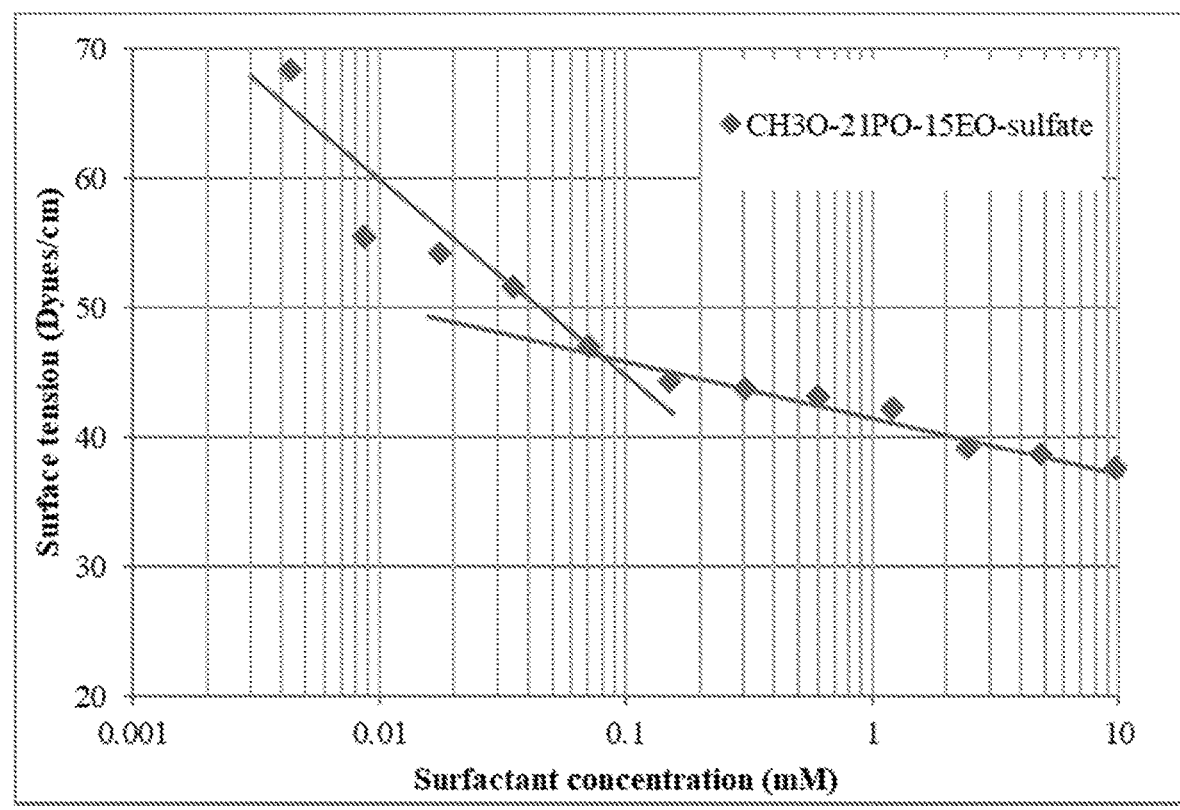
FIG. 3 depicts surface tension measurements of $CH_3O$-21PO-15EO-sulfate.

ST measurements of $CH_3O$-xPO-yEO-sulfate/carboxylate surfactants were performed, and compared with conventional surfactants. The results obtained for $CH_3O$-40PO-20EO-sulfate, $CH_3O$-40PO-20EO-carboxylate and $CH_3O$-60PO-30EO-carboxylate surfactants are shown in FIGS. 1 & 2. ST lowered to about 31-32 dynes/cm, and the CMC values were found to be about 0.01-0.02 mM. The ST lowered only to about 38 dynes/cm with $CH_3O$-21PO-15EO-sulfate, and the CMC value was found to be about 0.07 mM (FIG. 3).

Figure 4:
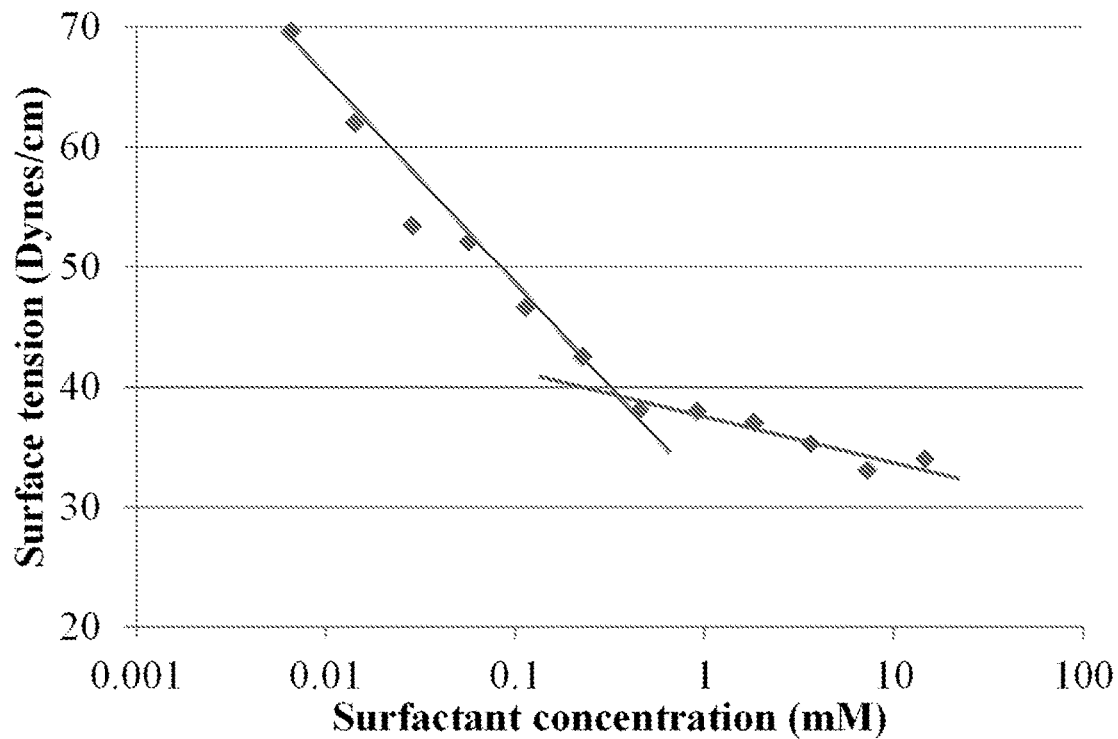
FIG. 4 depicts surface tension measurements of $C_{12-13}$-7PO-sulfate.
Figure 5:
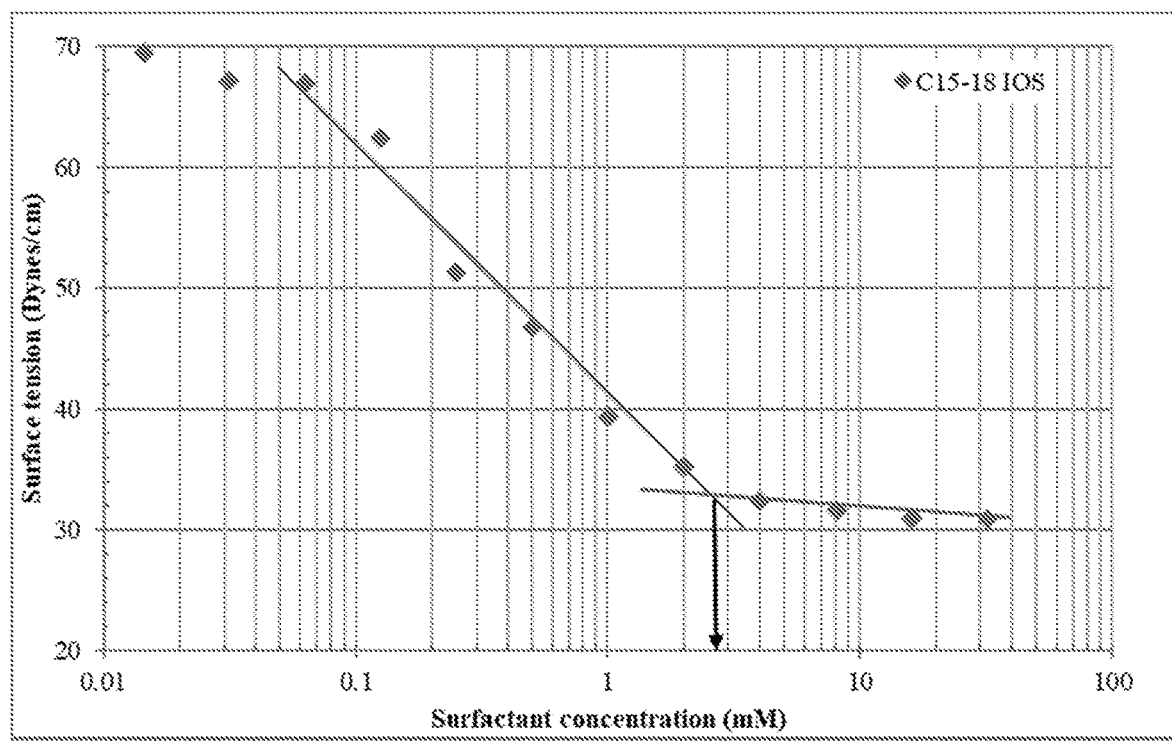
FIG. 5 depicts surface tension measurements of $C_{15-18}$ IOS.

Surface tension measurements of conventional surfactants were also performed to compare them with novel surfactants. ST data for $C_{12-13}$-7PO-sulfate and $C_{15-18}$ IOS are shown in FIGS. 4 & 5. The minimum ST values of these surfactants were found to be about 34 dynes/cm and 31 dynes/cm, respectively. Their CMC values were about 0.7 mM and 3 mM, respectively.

Figure 6:
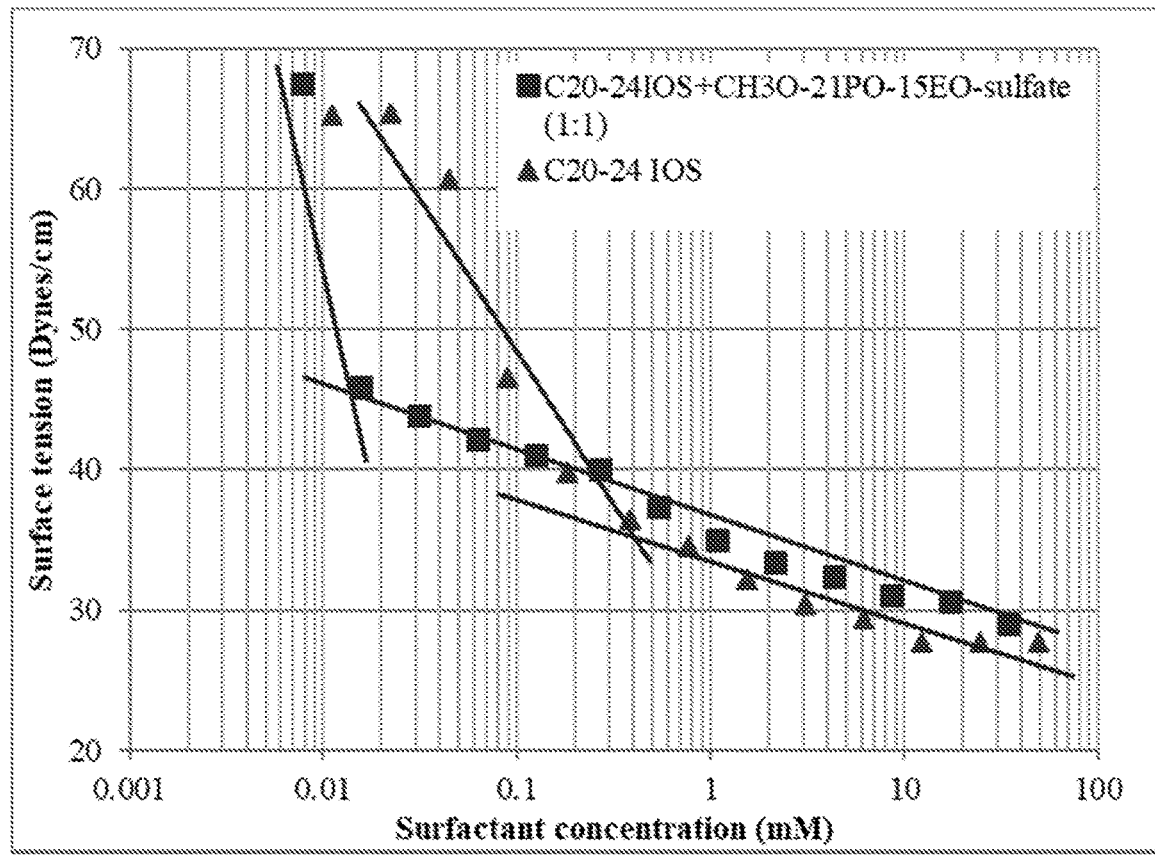
FIG. 6 depicts surface tension measurements of $C_{20-24}$ IOS and a 1:1 blend of $C_{20-24}$ MS with $CH_3O$-21PO-15EO-sulfate.

ST measurements were also performed for $C_{20-24}$ IOS and a 1:1 blend of $CH_3O$-21PO-15EO-sulfate with $C_{20-24}$ IOS (FIG. 6). $C_{20-24}$ IOS lowered surface tension to about 27 dynes/cm and showed a CMC value of about 0.4 mM. The blend also lowered the ST to about 29 dynes/cm and showed a CMC value of about 0.012 mM. Note that the CMC of the blend of $C_{20-24}$ IOS with $CH_3O$-21PO-15EO-sulfate was significantly lower than that of $C_{20-24}$ IOS. The ST lowered more when $CH_3O$-21PO-15EO-sulfate was blended with $C_{20-24}$ IOS, compared to just by itself (see FIG. 3).

Figure 7:
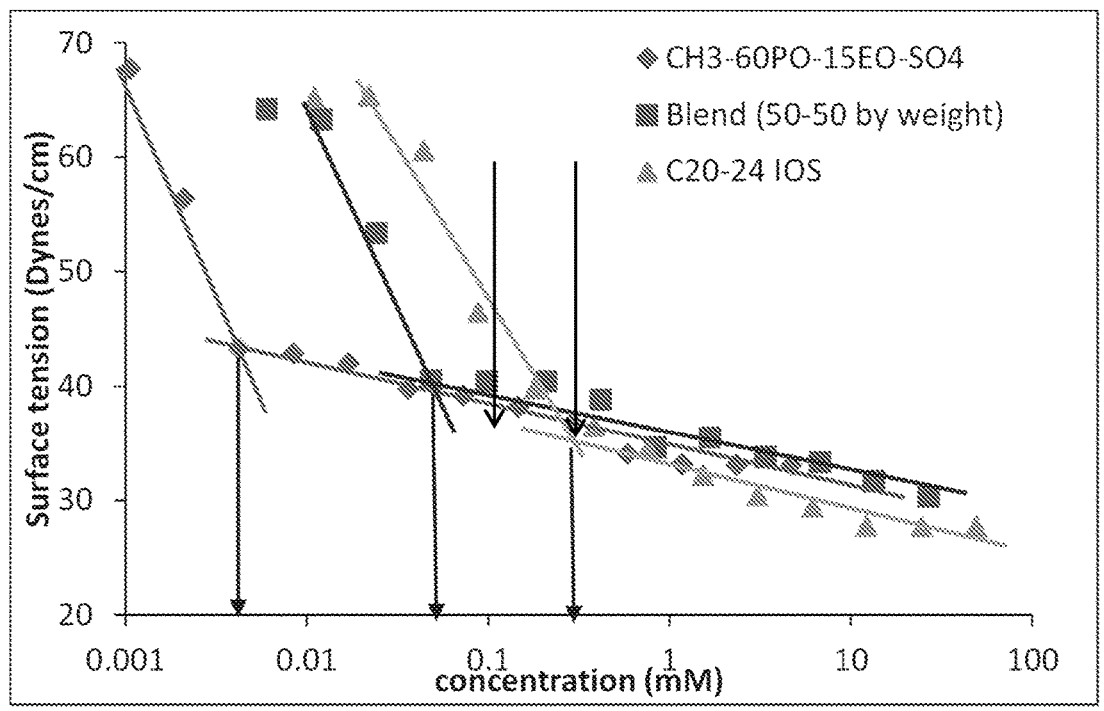
FIG. 7 depicts tension measurements of $CH_3O$-60PO-15EO-$SO_3Na$, $C_{20-24}$ IOS and 1:1 (wt:wt) blend.
Figure 8:
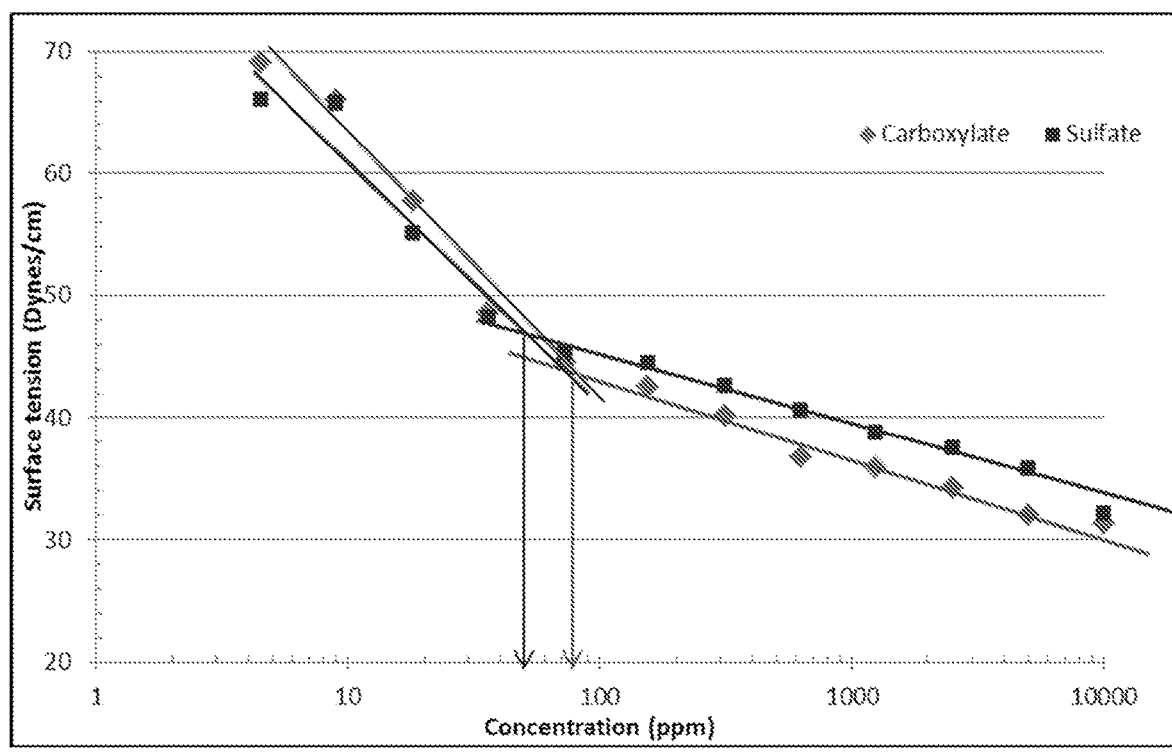
FIG. 8 depicts tension measurements of $CH_3$—O-60PO-30EO—COONa/$SO_4$.
Figure 9:
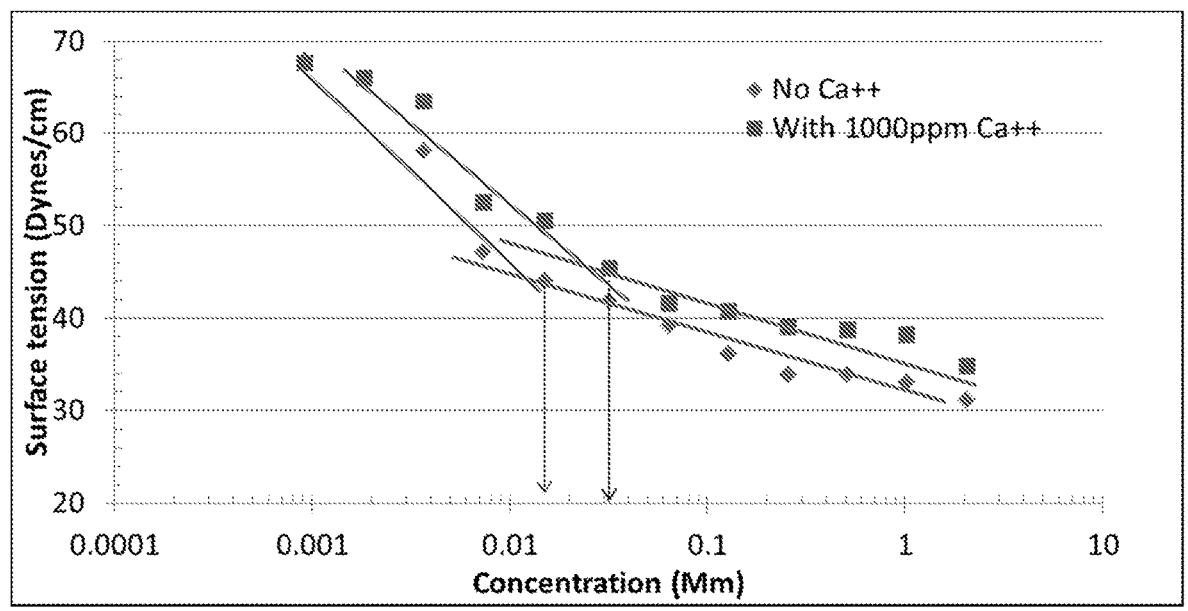
FIG. 9 depicts tension measurements of $CH_3$—O-60PO-30EO—$COO^-$ with and without calcium ions.
Figure 10:
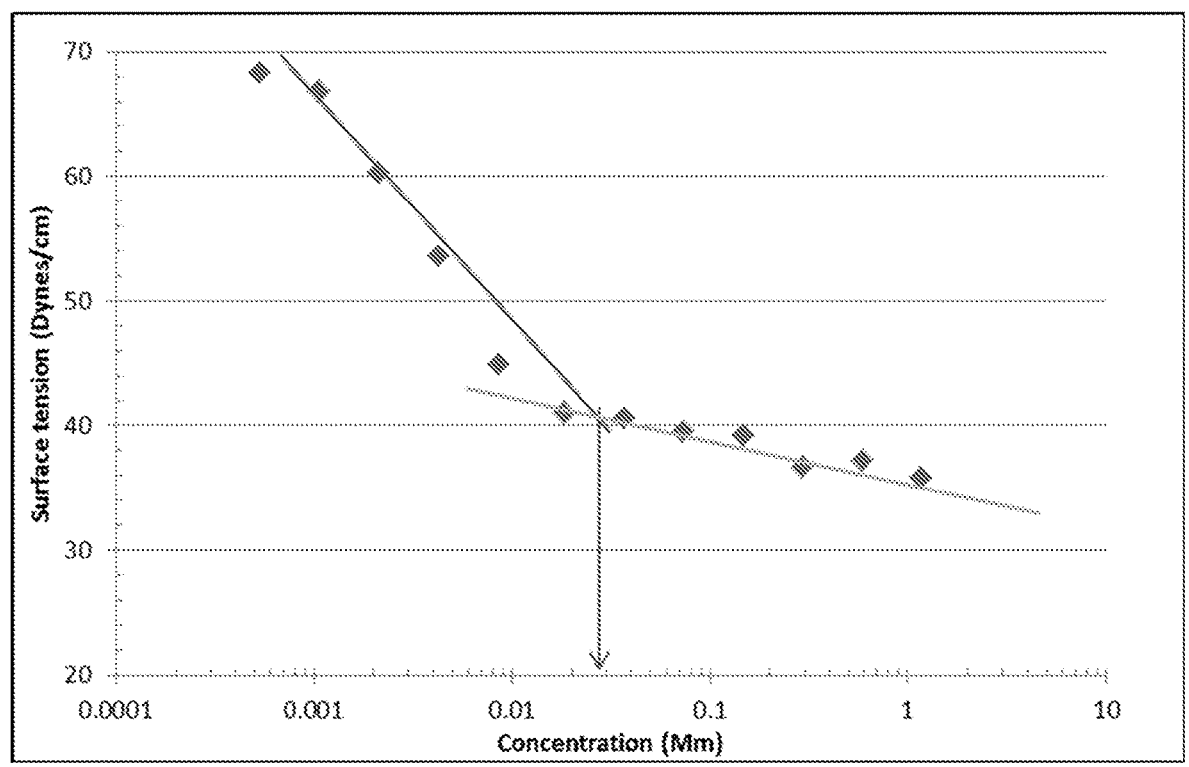
FIG. 10 depicts tension measurements of $CH_3$—O-70PO-100EO (Mm).
Figure 11:
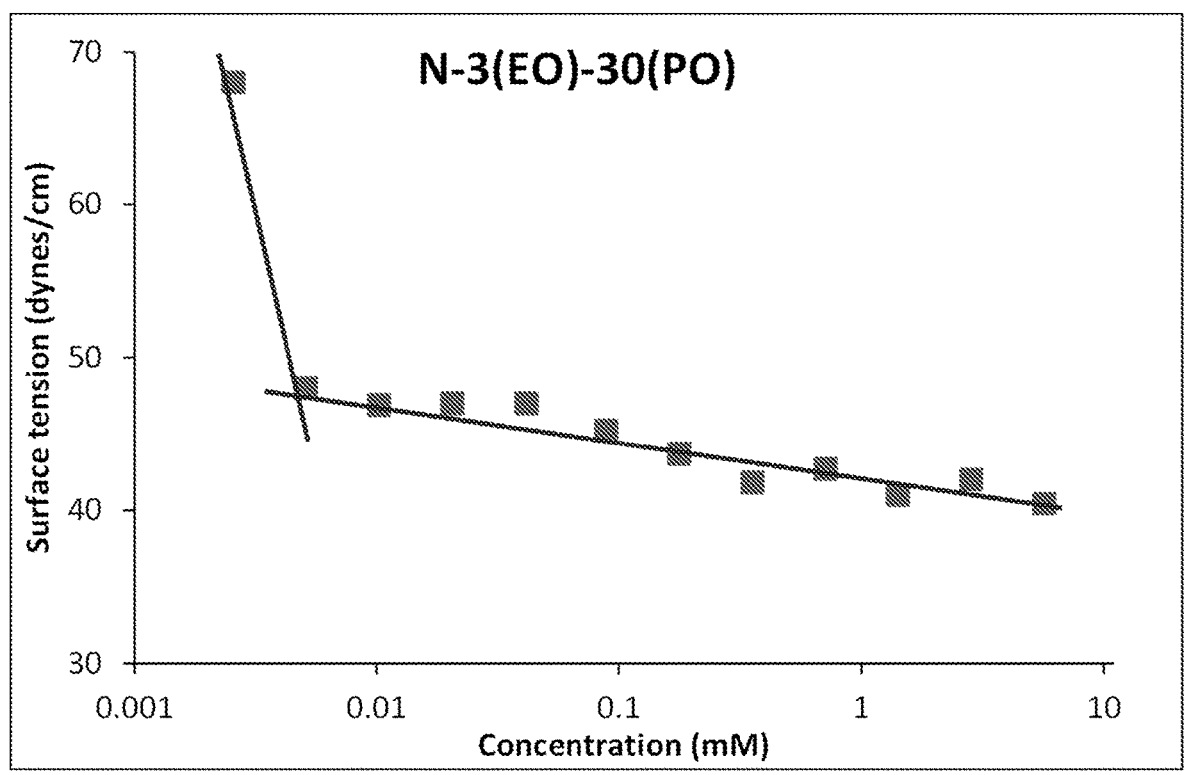
FIG. 11 depicts surface tension measurements of N-(EO-30PO)$_3$.

Additional surface tension measurements are shown in FIG. 7-FIG. 10 as follows:

| | |
|---|---|
| FIG. 7 | Surface tension measurements of $CH_3O$-60PO-15EO-$SO_3$Na, $C_{20-24}$ IOS and 1:1 (wt:wt) blend |
| FIG. 8 | Surface tension measurements of $CH_3$—O-60PO-30EO-COONa/$SO_4$ |
| FIG. 9 | Surface tension measurements of $CH_3$—O-60PO-30EO-COO$^-$ with and without calcium ions |
| FIG. 10 | Surface tension measurements of $CH_3$—O-70PO-100EO |
| FIG. 11 | Surface tension measurements of 2 wt % N-(EO-30PO)$_3$ |

Example 2

Aqueous Stability

A study was conducted to identify aqueous stability at various reservoir conditions of various surfactants. The assessment included conducting aqueous stability tests with these surfactant molecules, by themselves, and in combination with IOS and alkyl benzene sulfonate (ABS) surfactants at various temperatures. In these tests, aqueous solutions containing fixed amounts of surfactants (typically 1 wt %) were prepared, and salinity was systematically increased by adding sodium chloride (with and without hardness). Sodium carbonate was used for performing salinity scans in some cases. The salinity (and hardness) up to which the surfactant solutions remained clear (and single phase) at a given temperature is reported as the aqueous stability limit under those conditions. The samples were kept at different temperatures to study the effect of temperature on their stability. Experiments were repeated in presence of partially hydrolyzed polyacrylamide polymers in some cases.

Figure 12:
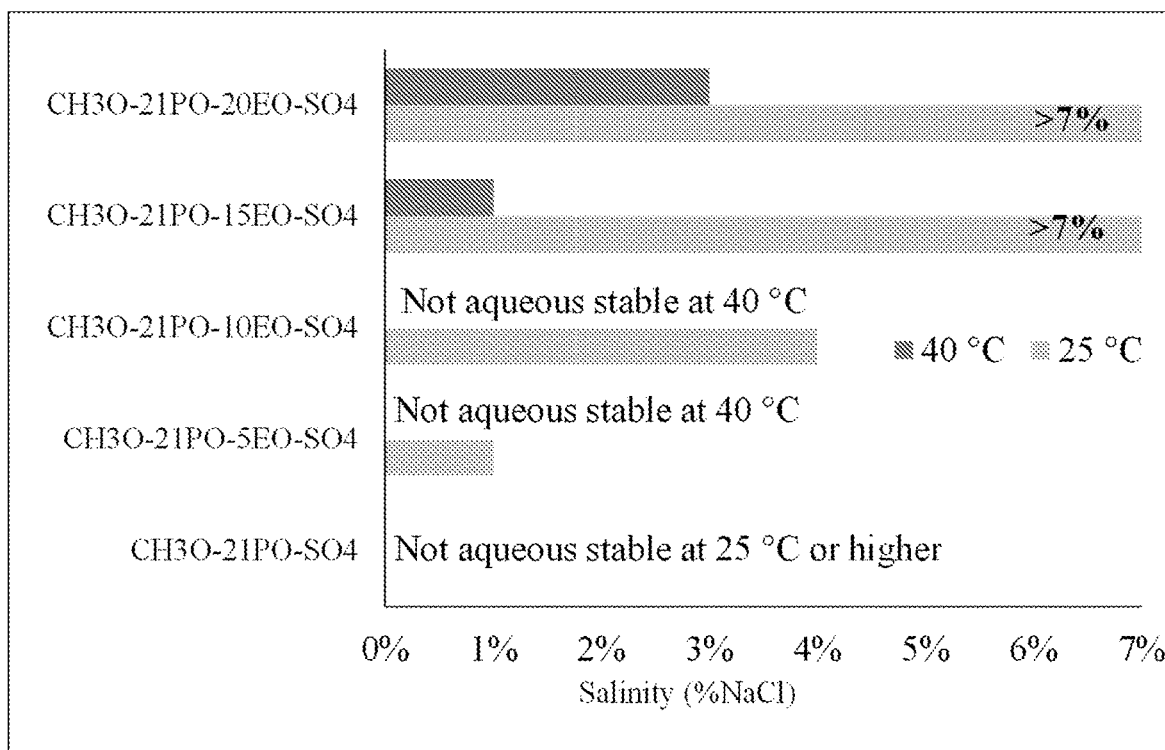
FIG. 12 depicts aqueous stability results of $CH_3O$-21PO-xEO-sulfate surfactants at 25° C. and 40° C.
Figure 13:
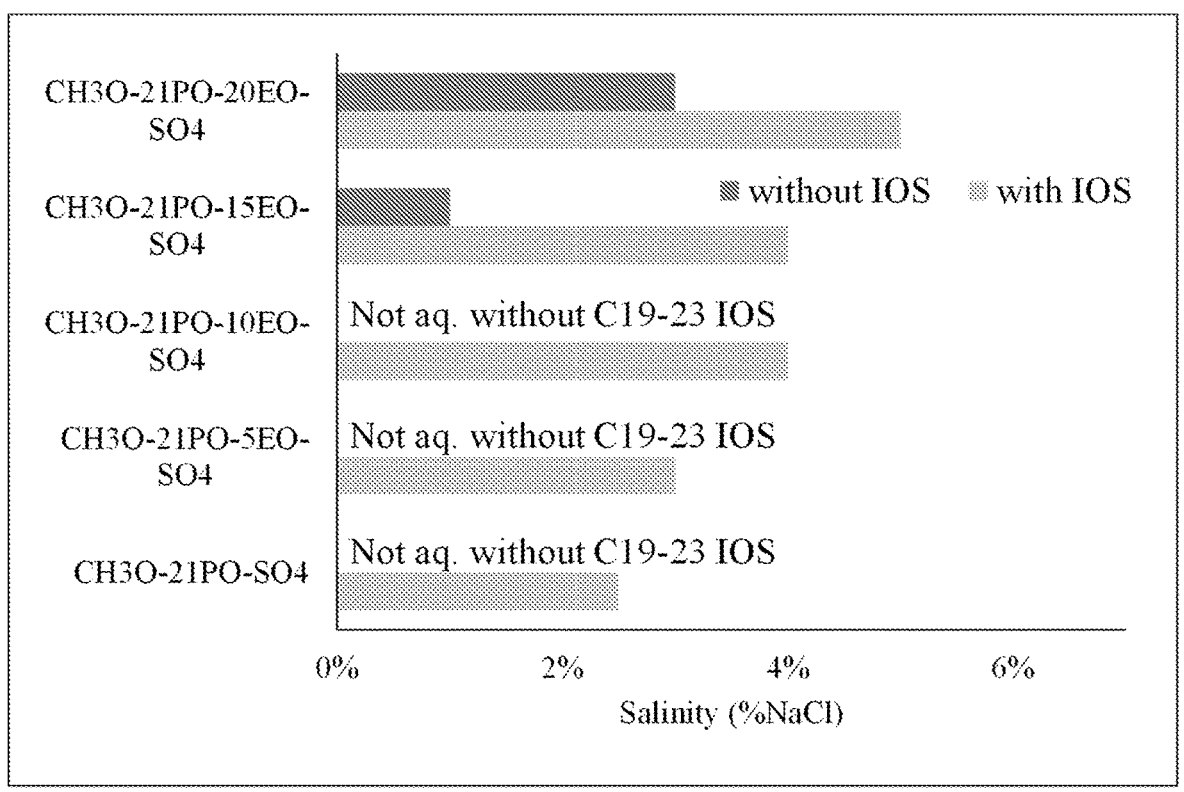
FIG. 13 depicts aqueous stability results of $CH_3O$-21PO-xEO-sulfate with $C_{19-23}$ IOS (0.5 wt % each) at 40° C.
Figure 14:
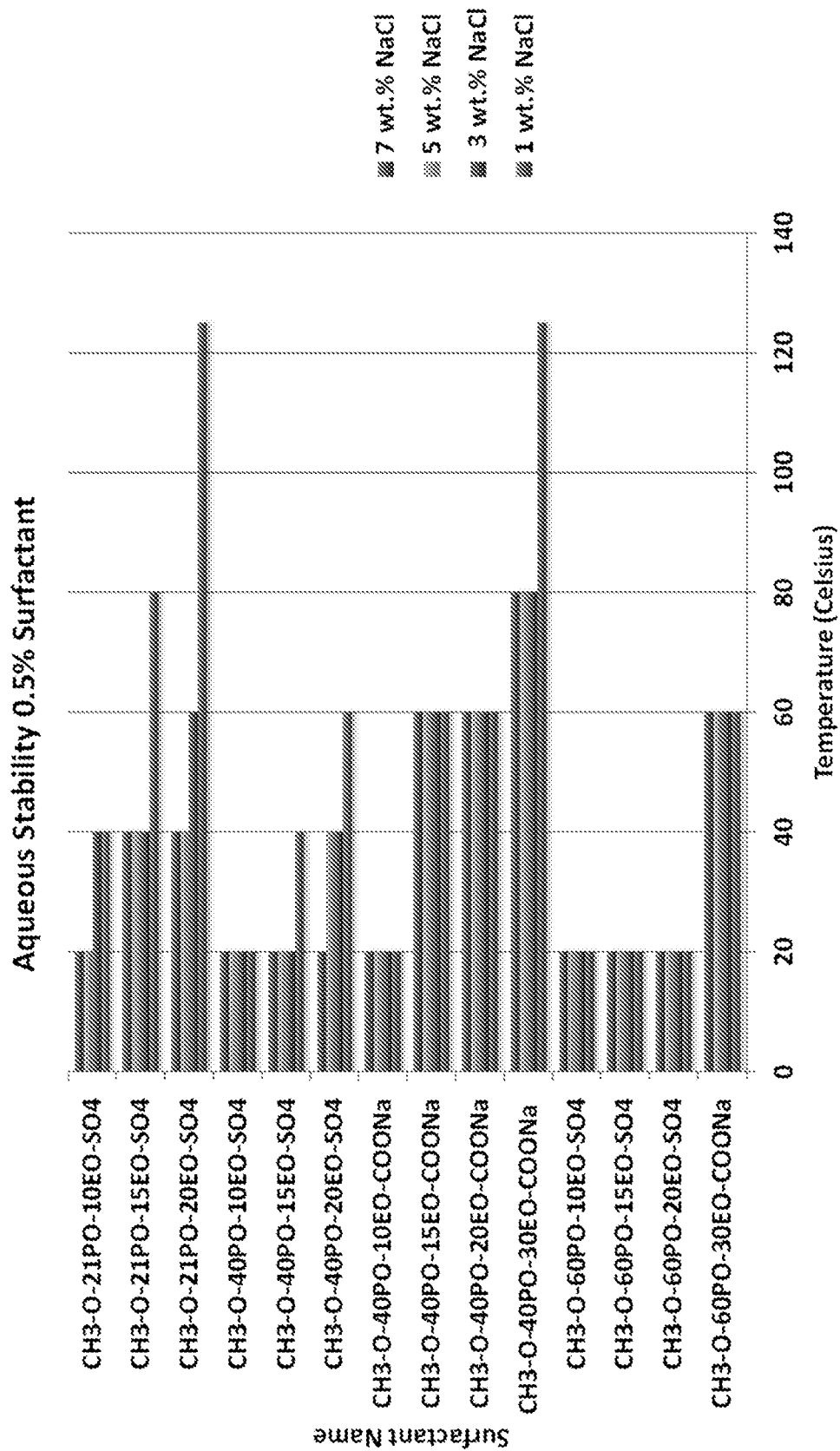
FIG. 14 depicts aqueous stability results of various surfactants at 0.5%.

Results obtained by using $CH_3O$-21PO-xEO-sulfate surfactants are presented in FIGS. 12 and 13. Similar experiments were also conducted with $CH_3O$-40PO-xEO-sulfate/carboxylate and $CH_3O$-60PO-xEO-sulfate/carboxylate surfactants, as shown in FIG. 14. Aqueous stability experiments showed that $CH_3O$-21PO-sulfate surfactant was not aqueous stable by itself even at room temperature (FIG. 12). However, addition of EO groups improved their aqueous stability. $CH_3O$-21PO-5EO-sulfate and $CH_3O$-21PO-10EO-sulfate surfactants were found to be aqueous stable up to 1 wt % NaCl and 4 wt % NaCl, respectively. Further addition of EO groups showed better aqueous stability results (>7 wt % NaCl). The experiments were repeated at 40° C. to study the effect of temperature. Lower aqueous stability, as compared to 25° C., was observed at 40° C. due to the increased hydrophobicity of PO groups with increasing temperature. The aqueous stability of these surfactants improved greatly when they were blended with TOS surfactants (FIG. 13). These results shown in FIG. 13 were obtained by blending $CH_3O$-21PO-xEO-sulfate surfactants with $C_{19-23}$ IOS. From FIG. 13, it can be seen that the blend showed better aqueous stability due to good synergy.

Aqueous stability experiments were performed for Amino-n(PO) surfactants, using triethanolamine. 1 wt % surfactant was added to DI water and equilibrated at various temperatures. The surfactant solution was found to be aqueous stable up to 30 POs at room temperature. However, in acidic conditions, the surfactant solutions containing up to 75 POs were found to be aqueous stable in DI water.

Figure 15:
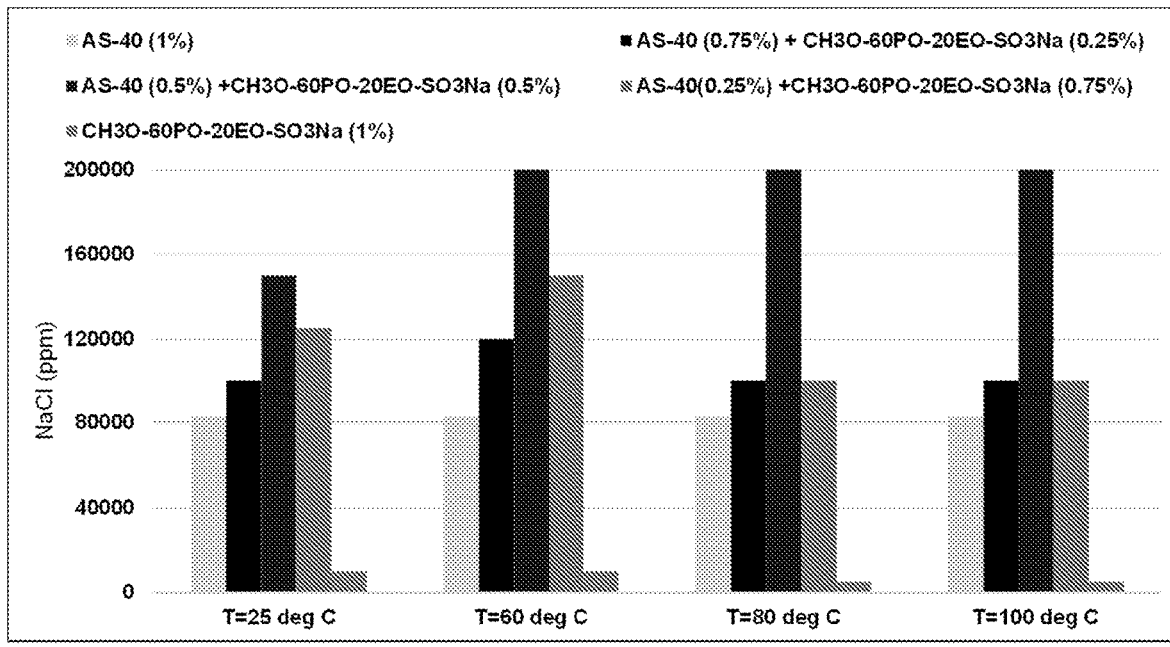
FIG. 15 depicts aqueous stability results of AS-40 ($C_{14-16}$ AOS) and $CH_3$—O-60PO-20EO—$SO_3$.
Figure 16:
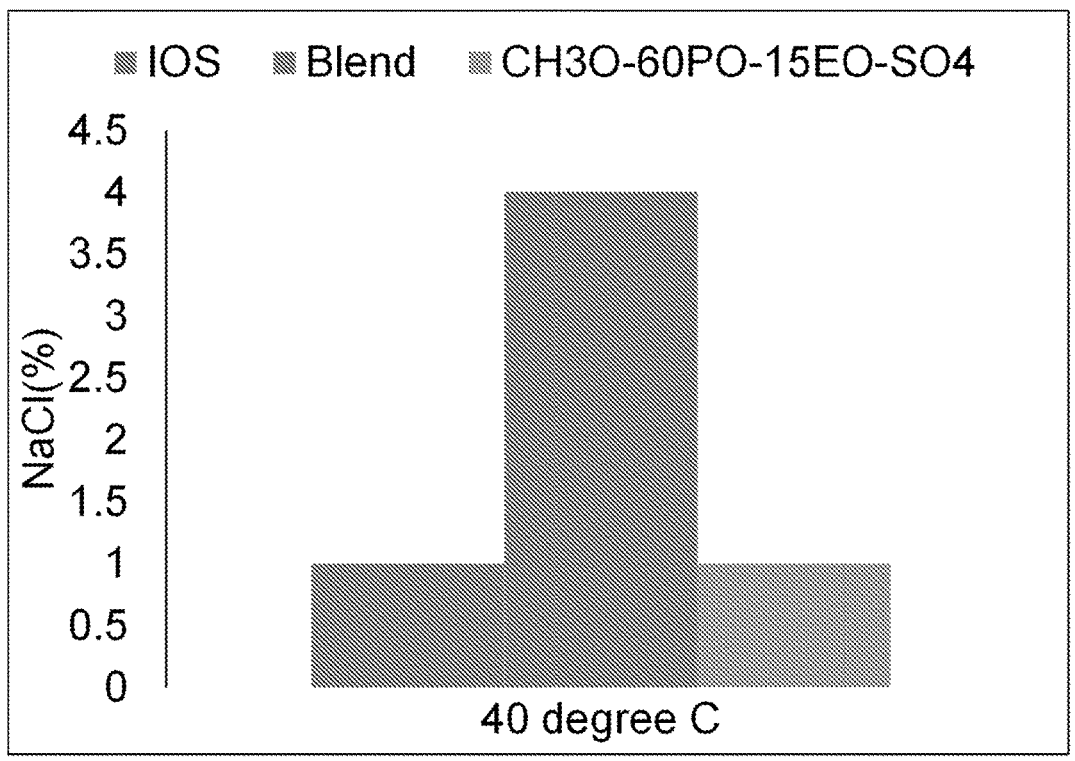
FIG. 16 depicts aqueous stability results of $CH_3O$-60PO-15EO—$SO_3Na$, $C_{20-24}$ MS and 1:1 blend.
Figure 17:
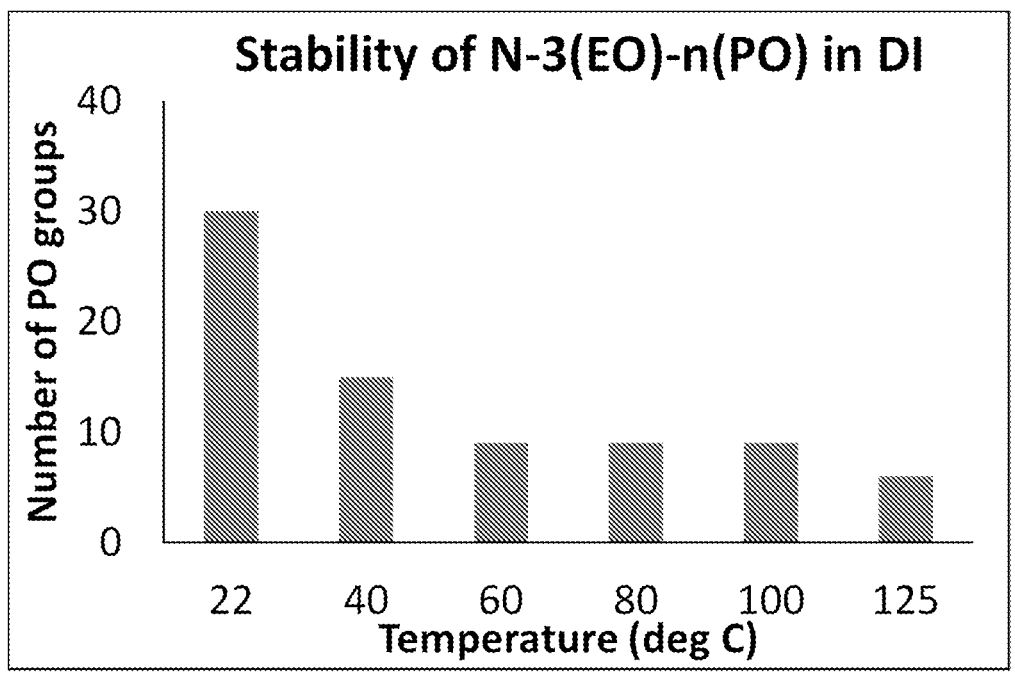
FIG. 17 depicts aqueous stability results of N-(EO—POy)$_3$.

FIGS. 15-17 and Table 2 show additional aqueous stability data.

TABLE 1

FIGS. 15-17.

| | |
|---|---|
| FIG. 15 | Aqueous stability results of AS-40 ($C_{14-16}$ AOS) and $CH_3$—O-60PO-20-$EOSO_3$ |
| FIG. 16 | Aqueous stability results of $CH_3O$-60PO-15EO-$SO_3Na$, $C_{20-24}$ IOS and 1:1 blend |
| FIG. 17 | Aqueous stability results of Aqueous stability results of N-(EO-nPO)$_3$ |

TABLE 2

Aqueous stability data.

| | | 0.5% Surfactant | | | | |
|---|---|---|---|---|---|---|
| Surfactant | % wt. NaCl | RT | 50 C. | 65 C. | 80 C. | 90 C. |
| $CH_3$—O-70PO-30EO | 1 | Clear | Hazy | Ppt | Ppt | Ppt |
| | 2 | S. Hazy | Hazy | Ppt | Ppt | Ppt |
| | 3 | S. Hazy | Hazy | Ppt | Ppt | Ppt |
| | 4 | S. Hazy | Hazy | Ppt | Ppt | Ppt |
| $CH_3$—O-70PO-45EO | 1 | Clear | V. S. hazy | V. S. hazy | Ppt | Ppt |
| | 2 | Clear | V. S. hazy | V. S. hazy | Ppt | Ppt |
| | 3 | Clear | V. S. hazy | V. S. hazy | Ppt | Ppt |
| | 4 | Clear | V. S. hazy | V. S. hazy | Ppt | Ppt |
| $CH_3$—O-70PO-75EO | 1 | Clear | Clear | Clear | v. s. hazy | Ppt |
| | 2 | Clear | Clear | Clear | v. s. hazy | Ppt |
| | 3 | Clear | Clear | Clear | v. s. hazy | Ppt |
| | 4 | Clear | Clear | v. s. hazy | s. hazy | Ppt |
| $CH_3$—O-70PO-100EO | 1 | Clear | Clear | Clear | Clear | Thick, micelle |
| | 2 | Clear | Clear | Clear | Clear | Thick, micelle |
| | 3 | Clear | Clear | Clear | Clear | Hazy |
| | 4 | Clear | Clear | Clear | v. s. hazy | Hazy |

Example 3

Surfactant Phase Behavior

Surfactant phase behavior experiments were conducted with various crude oils to investigate if ultralow IFT values were achieved using these surfactants by themselves and in combination with IOS (and ABS) surfactants at various temperatures. These experiments were conducted by first preparing a given amount of aqueous solutions, as was described previously, in graduated glass pipettes. The aqueous levels were recorded. A given amount of oil was then added to these samples and the glass tubes were sealed. The samples were allowed to equilibrate at a given temperature and mixed from time to time. The samples were then inspected visually for low IFT regions. Oil and water solubilization ratios were calculated based on their amounts solubilized which was later used to estimate the IFT values. IFT values were measured by using a Krüss spinning drop tensiometer in some cases.

Initially, the novel surfactants were used by themselves. Phase behavior tubes obtained with 1 wt % $CH_3O$-60PO-30EO-carboxylate surfactant were measured using the Krüss spinning drop tensiometer and were found to be as low as 0.005 dynes/cm. These surfactants themselves lowered the IFT significantly with the crude oil and were aqueous stable up to 4% NaCl.

Figure 18:
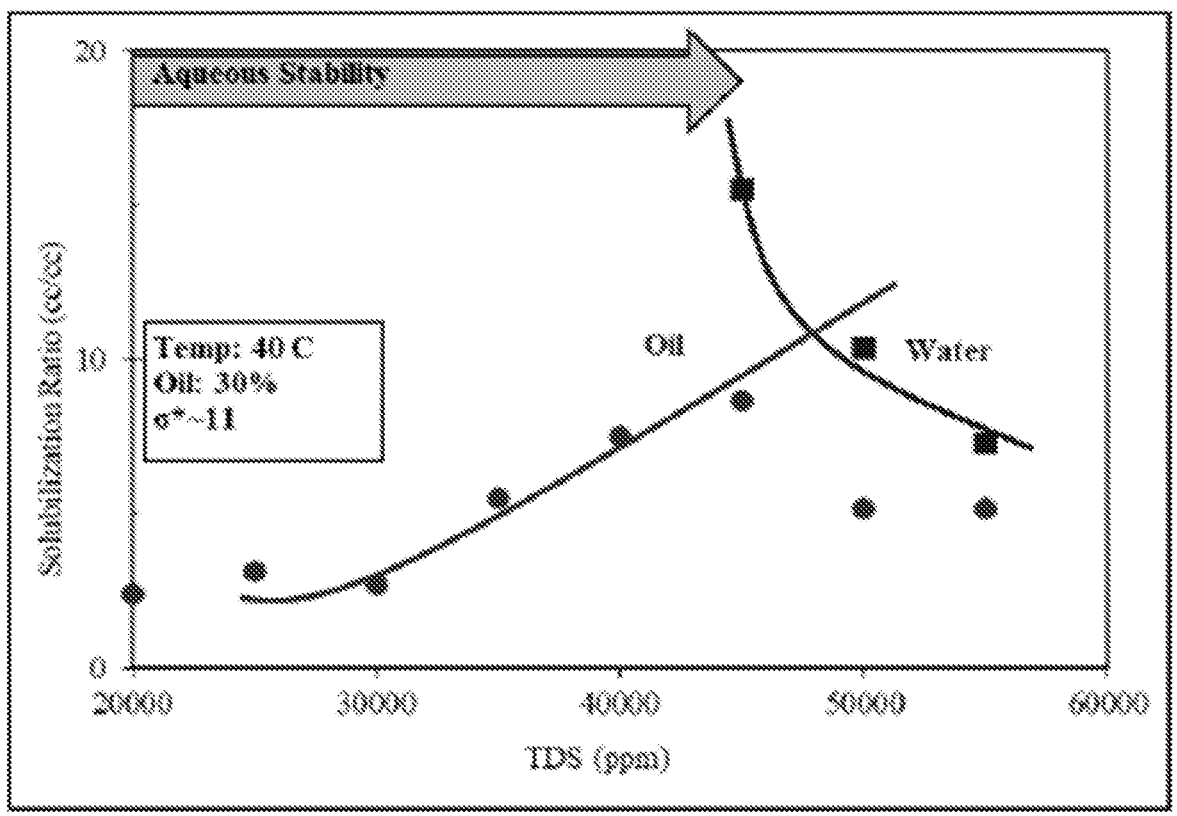
FIG. 18 depicts solubilization ratios for phase behavior tubes of 0.5% $CH_3$—O-21PO-10EO-sulfate, 0.5% $C_{19-23}$ IOS, 1% TEGBE at 40° C.

As ultralow IFT was not observed by using the new surfactants alone, they were blended with IOS surfactants in subsequent phase behavior experiments. These experiments were performed at 40° C. and 65° C. Ultralow IFT with crude oil was observed around 3.25-3.5 wt % NaCl at 40° C. when the surfactant blend consisted of 0.5 wt % $CH_3O$-21PO-10EO-sulfate and 0.5 wt % $C_{20-24}$ IOS. The formulation, however, was aqueous stable only up to 1.5 wt % NaCl. The phase behavior was therefore repeated by replacing $C_{20-24}$ IOS with $C_{19-23}$ IOS. This resulted in greatly improving the aqueous stability, in addition to showing ultralow IFT. In this case, ultralow IFT was observed at about 4.5 wt % NaCl. The aqueous stability was observed up to about 4 wt % NaCl. The formulation, however, showed viscous emulsions in Winsor type II region. A cosolvent (1 wt % TEGBE) was therefore added to the surfactant formulation (FIG. 18). This resulted in greatly improving the fluidity of the samples in addition to also improving aqueous stability slightly. The surfactant formulation gave a solubilization ratio of about 11 cc/cc at the optimum salinity (4.5 wt % NaCl) and was also aqueous stable (see FIG. 18).

Figure 19:
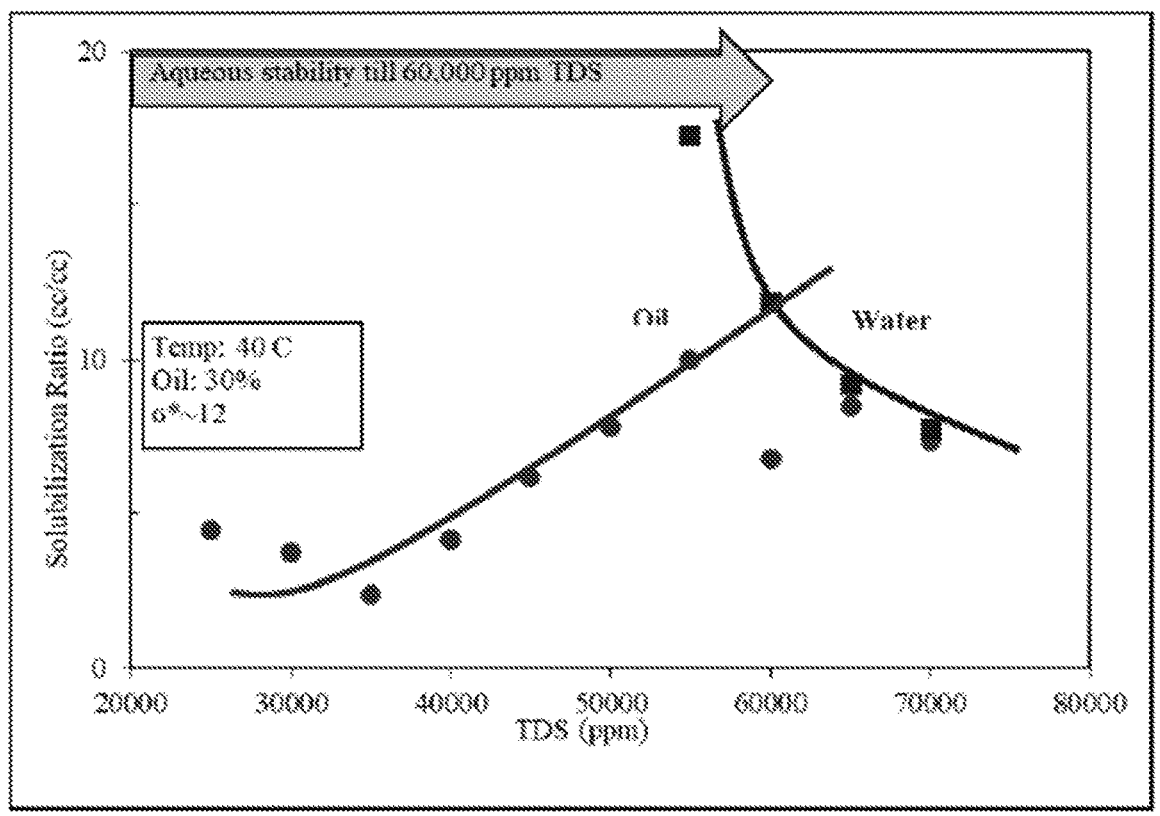
FIG. 19 depicts solubilization ratios for phase ultraflow IFT tubes of 0.5% $CH_3$—O-21PO-10EO sulfate, 0.5% $C_{19-23}$ IOS, 1% TEGBE at 40° C.

An alkali surfactant polymer (ASP) formulation was also developed by using 0.5 wt % $CH_3O$-21PO-10EO-sulfate, 0.5 wt % $C_{19-23}$ IOS and 1 wt % TEGBE (FIG. 19) at 40° C. In this formulation, salinity scan was performed by adding $Na_2CO_3$ to 2.0 wt % NaCl base brine. Ultralow IFT was observed between 5.5-6.5 wt % TDS, and a solubilization ratio of 12 cc/cc was obtained at the optimum salinity. Note that these samples equilibrated much faster due to the presence of an alkali.

Figure 20:
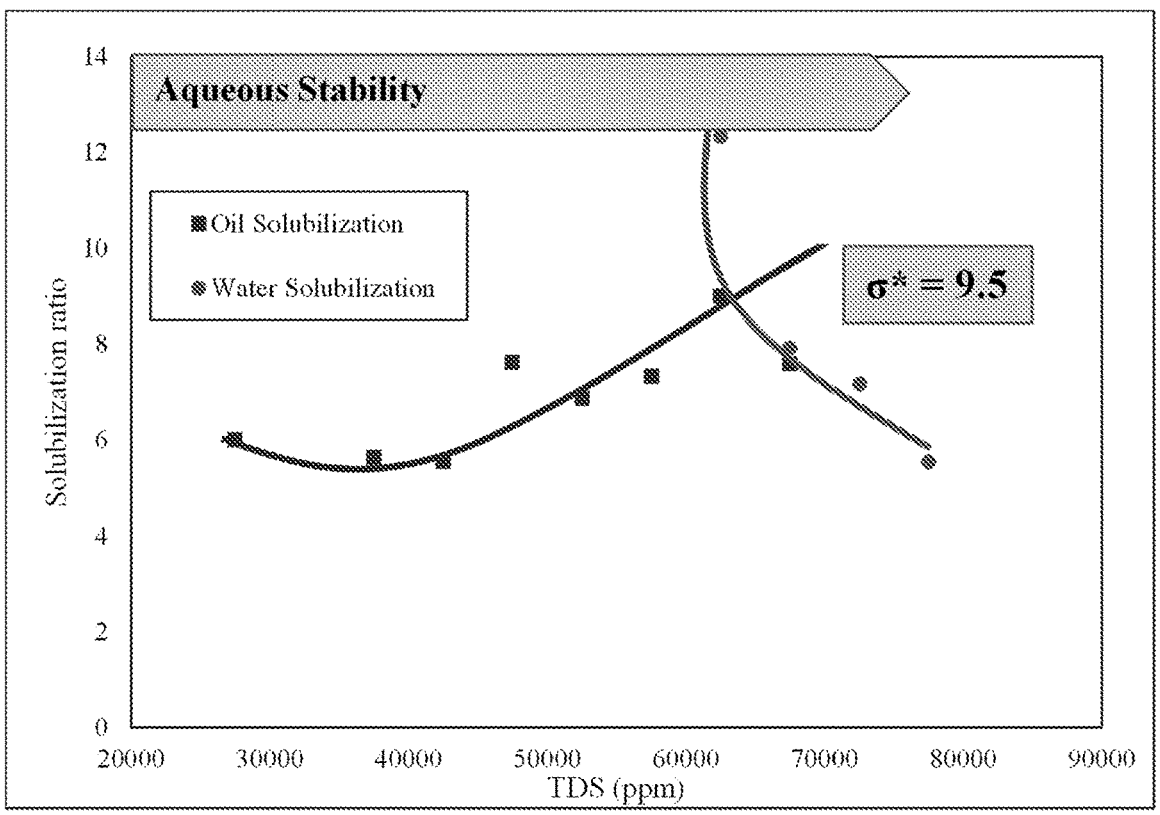
FIG. 20 depicts solubilization ratios for phase behavior tubes of 0.4% $CH_3$—O-60PO-20EO carboxylate, 0.6% $C_{15-18}$ MS at 65° C.

Phase behavior experiments were also conducted to obtain ultralow IFT SP formulation for a hard brine system consisting of 65,000 ppm TDS and 2,200 ppm hardness at 65° C. The surfactant formulation consisted of 0.4 wt % $CH_3O$-60PO-20EO-carboxylate and 0.6 wt % $C_{15-18}$ IOS. The formulation showed ultralow IFT and was aqueous stable up to 75,000 ppm TDS. The solubilization plot for this formulation is shown in FIG. 20 and the estimated IFT at the optimal salinity was about 0.004 dynes/cm.

Comparison of Novel Surfactants with Existing Surfactants

Figure 21:
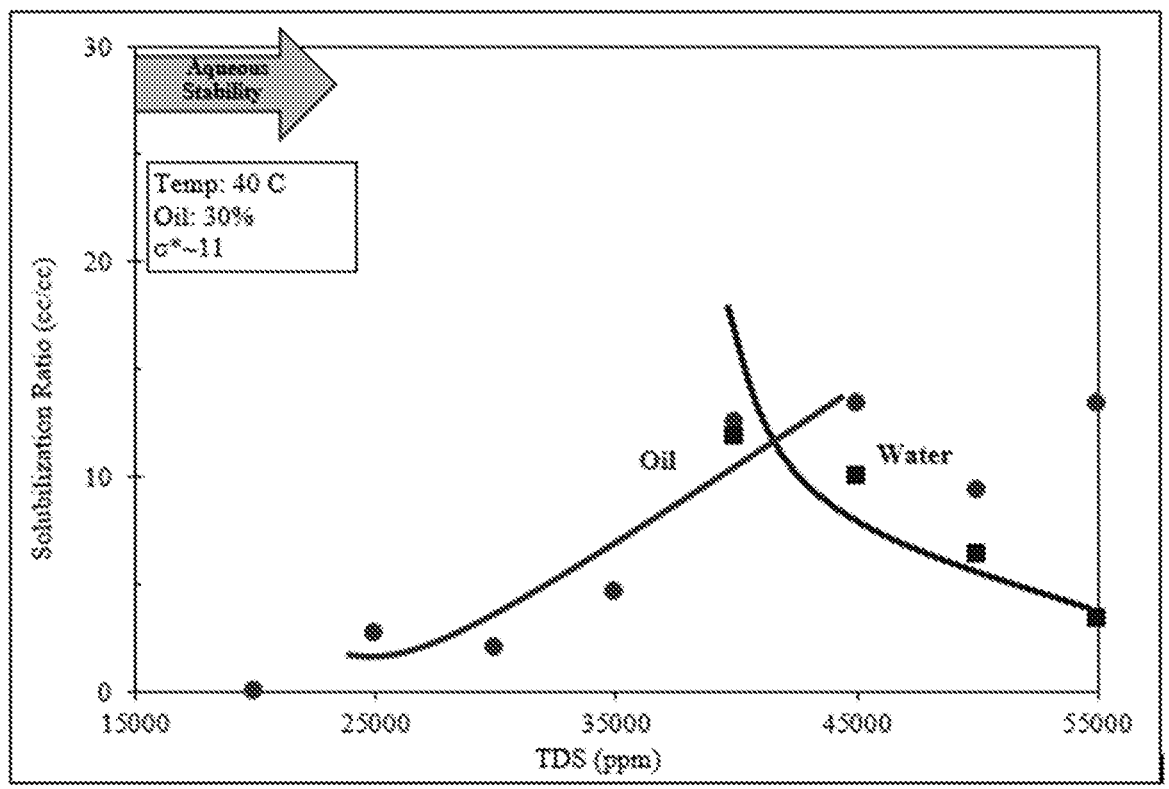
FIG. 21 depicts solubilization ratios for phase behavior tubes of 0.5% $CH_3$—O-21PO-sulfate, 0.5% $C_{19-23}$ IOS, 1% TEGBE.
Figure 22:
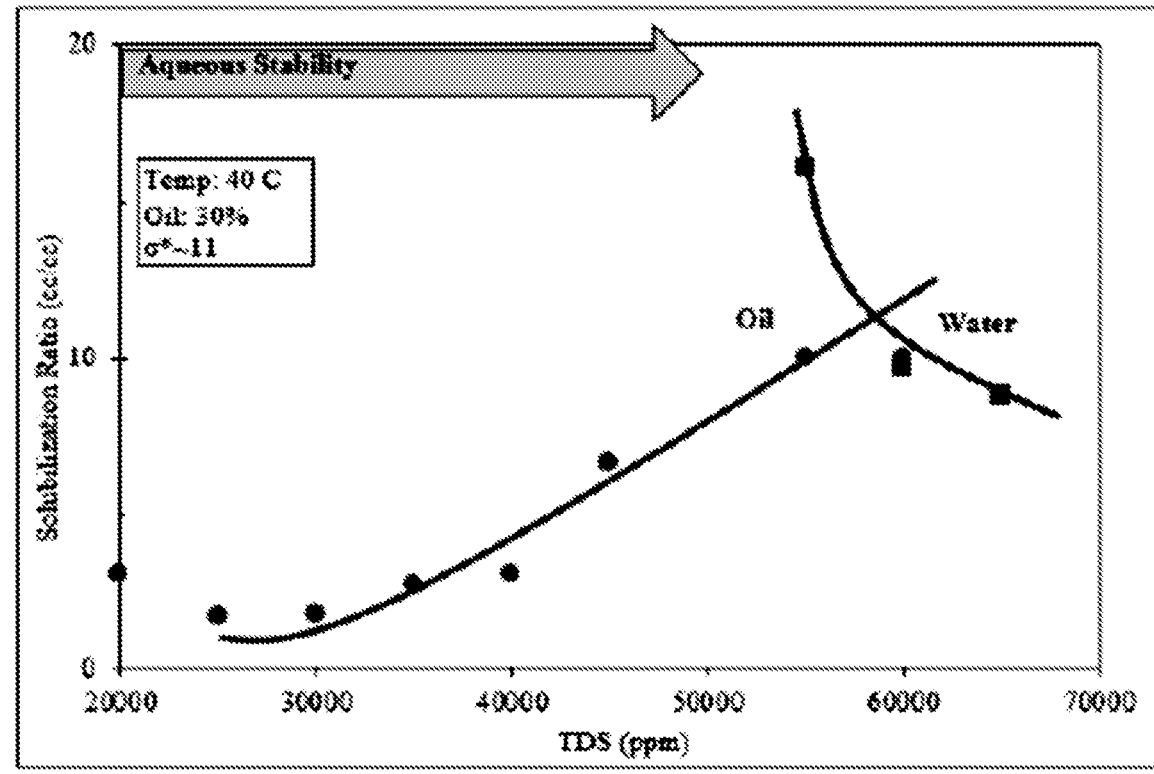
FIG. 22 depicts solubilization ratios for phase behavior tubes of 0.5% $C_{12-13}$-7PO-sulfate, 0.5% $C_{19-23}$ MS.

Additional phase behavior experiments were performed to compare the performance of novel surfactants with conventional ones for a given crude oil. Experiments were performed at 40° C. with soft brine and at 65° C. with high salinity/hardness brine. A comparison between $CH_3O$-21PO—$SO_4$ surfactant with $C_{12-13}$-7PO—$SO_4$ and $C_{12-13}$-13PO—$SO_4$ was made. Surfactant phase behavior experiments were performed with the same crude oil at 40° C. using 0.5 wt % of these surfactants in combination with 0.5 wt % $C_{19-23}$ IOS. The results obtained by using 0.5 wt % $CH_3O$-21PO—$SO_4$, 0.5 wt % $C_{19-23}$ IOS and 1 wt % TEGBE are shown in FIG. 21. The optimum salinity for this surfactant formulation was obtained at about 4.0 wt % NaCl and the corresponding solubilization ratio was about 11 cc/cc. The formulation did not have the aqueous stability at the optimum salinity. However, replacing $CH_3O$-21PO—$SO_4$ with $CH_3O$-21PO-10EO-$SO_4$ gave similar phase behavior with the crude oil (optimum salinity-4.5 wt % NaCl) in addition to aqueous stability up to the optimum salinity (see FIG. 18). The results obtained with 0.5 wt % $C_{12-13}$-7PO—$SO_4$ and 0.5 wt % $C_{19-23}$ IOS are shown in FIG. 22. It can be seen that the optimum salinity for this formulation was at about 5.75 wt % NaCl and the corresponding solubilization ratio was about 11 cc/cc. The aqueous stability limit of the surfactant formulation was slightly less than the optimum salinity. Similar experiment using 0.5 wt % $C_{12-13}$-13PO—$SO_4$ and 0.5 wt % $C_{19-23}$ IOS showed ultralow IFT at around 3.5 wt % NaCl and aqueous stability up to about 4.5 wt % NaCl. The solubilization ratios could not be obtained for these samples due to a long equilibration time.

Similarly, additional phase behavior experiments were performed to compare new surfactants with conventional surfactants at 65° C. with high salinity/hardness brine. The surfactant blends in these experiments consisted of 0.5 wt % of new (or conventional) surfactant and 0.5 wt % $C_{15-18}$ IOS. The conventional surfactants were chosen such that they closely resembled the novel surfactant they were compared with. Unlike the novel surfactant, the conventional surfactant contained a hard hydrophobe chain of 18 and 28 carbons, respectively.

Figure 23:
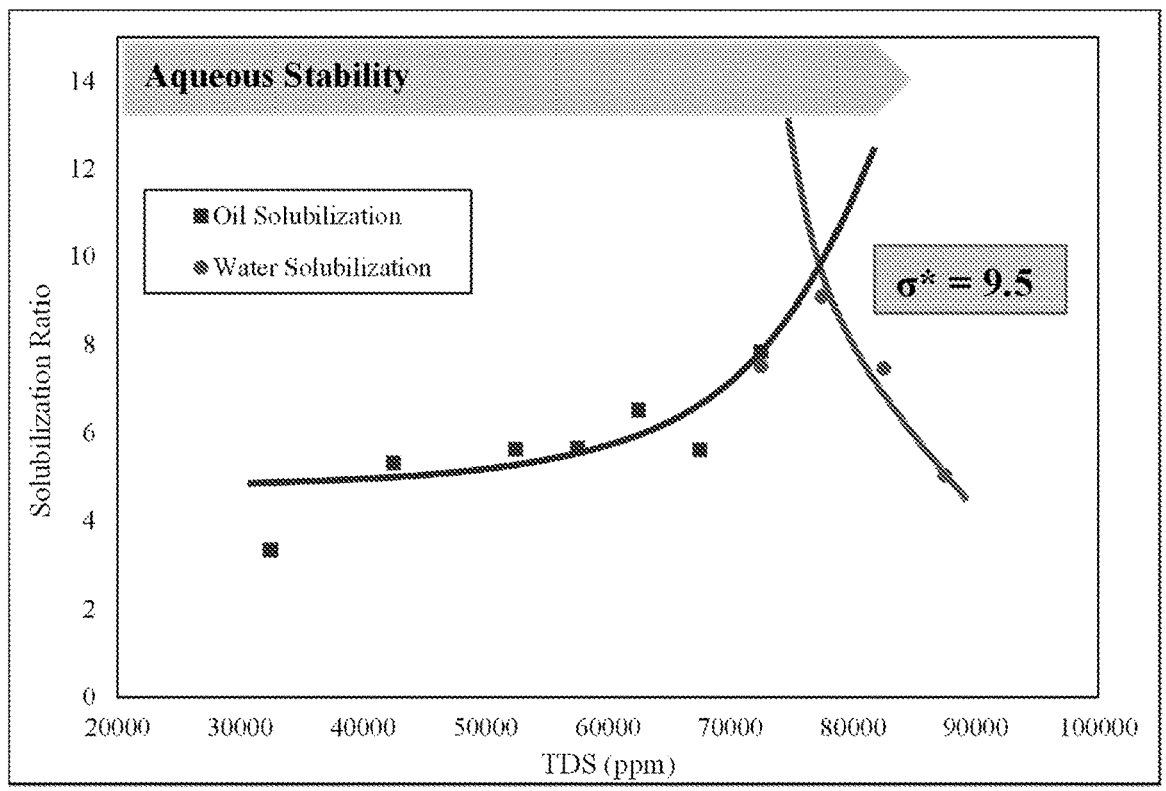
FIG. 23 depicts solubilization ratios for phase behavior tubes of 0.5% $CH_3$—O-60PO-30EO-carboxylate, 0.5% $C_{15-18}$ MS at 65° C.
Figure 24:
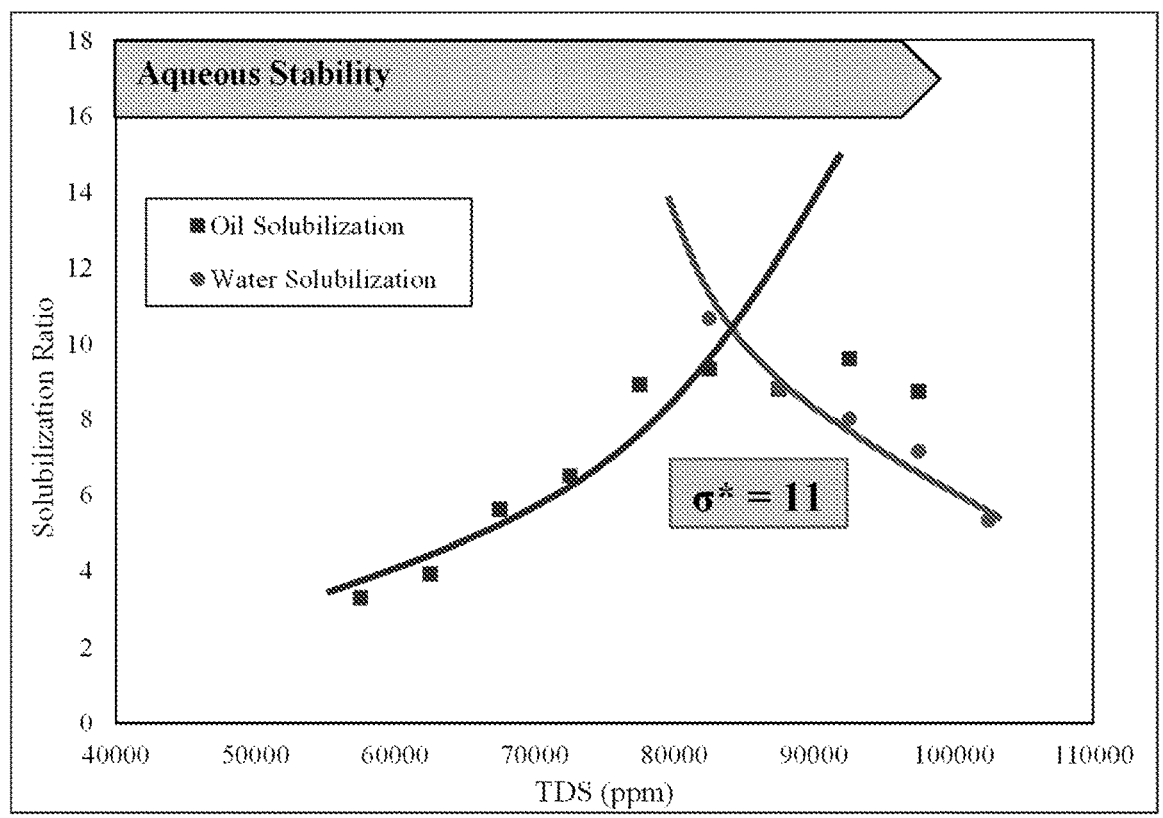
FIG. 24 depicts solubilization ratios for phase behavior tubes of 0.5% $C_{18}$-45PO-30EO-carboxylate, 0.5% $C_{15-18}$ MS at 65° C. The $C_{18}$ is oleyl based, having a bent double bond, which results in extra-large hydrophobe behavior.

Phase behavior experiment with 0.5 wt % $CH_3O$-60PO-30EO-carboxylate and 0.5 wt % $C_{15-18}$ IOS showed classical behavior at harsh reservoir conditions with ultralow IFT region between 72,500 77,500 ppm TDS with 2,500 ppm hardness, as shown in FIG. 23. The aqueous stability limit of this formulation was about 90,000 ppm at the reservoir conditions. The estimated IFT value at the optimal salinity was about 0.003 dynes/cm based on the solubilization ratio. Similarly, additional experiments were performed by replacing the novel surfactant with the conventional surfactants of varying hydrocarbon chain lengths. First, experiment was performed with 0.5 wt % oleyl-based $C_{18-45}$PO-30EO-carboxylate and 0.5 wt % $C_{15-18}$ IOS which showed ultralow IFT region between 82,500 97,500 ppm TDS with 3,150 ppm hardness, as shown in FIG. 24. Note that the $C_{18}$ group on the surfactant is oleyl based, with a bent double bond in the middle, which makes it behave like an extra-large hydrophobe. The aqueous stability limit of this formulation was about 100,000 ppm TDS at the reservoir condition. The estimated IFT value at the optimal salinity was about 0.002 dynes/cm.

Figure 25:
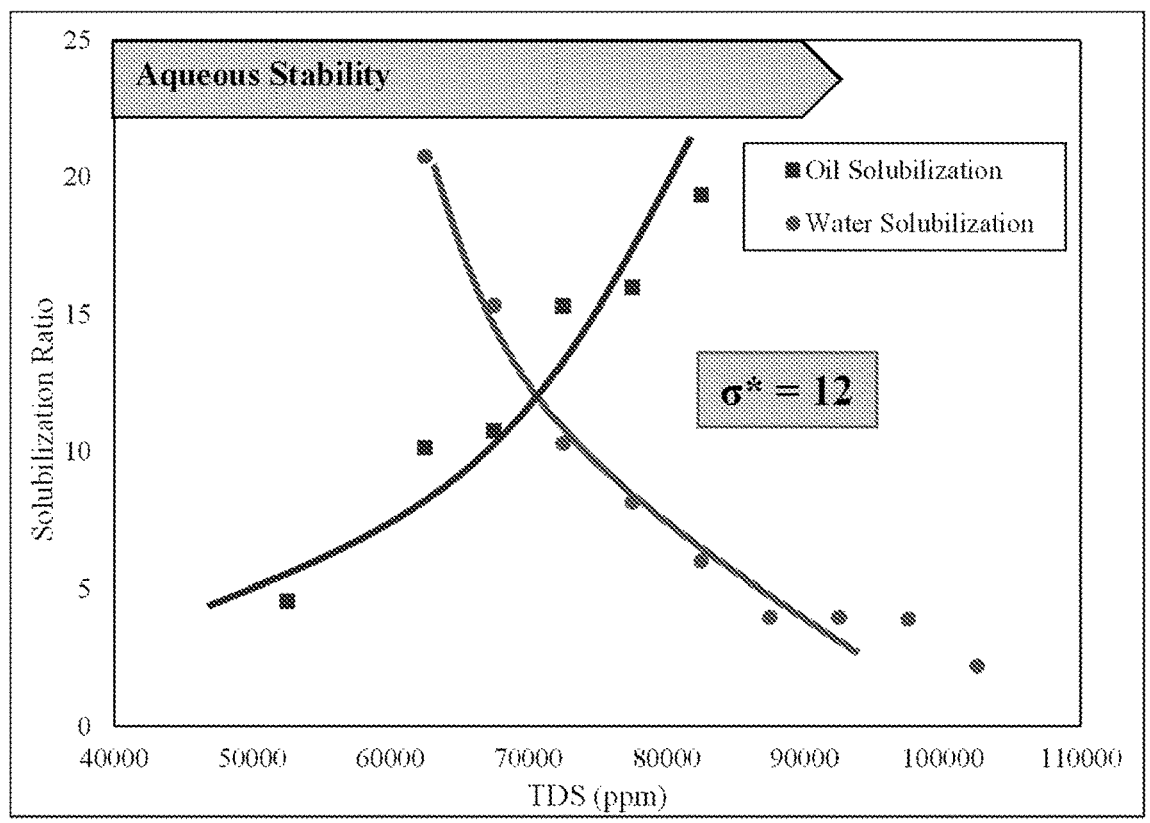
FIG. 25 depicts solubilization ratios for phase behavior tubes of 0.5% $C_{28}$-45PO-30EO-carboxylate, 0.5% $C_{15-18}$ MS at 65° C.

Another experiment was performed with 0.5 wt % $C_{28-45}$PO-30EO-carboxylate and 0.5 wt % $C_{15-18}$ IOS which showed ultralow IFT region between 62,500 72,500 ppm TDS with 2,300 ppm hardness, as shown in FIG. 25. The aqueous stability limit for this formulation was about 90,000 ppm at the reservoir conditions. The estimated IFT value at the optimal salinity was about 0.002 dynes/cm. This comparative study shows that the PO groups at higher temperature become more hydrophobic than the hydrocarbon chains, and lowers the optimal salinity. The solubilization ratios of about 9-9.5 were observed at the optimum salinity using the blend of new surfactants with IOS. Note that the solubilization ratios at the respective optimum salinities were about 11-12 using conventional surfactants due to the presence of hydrocarbon chains. Note that all three formulations discussed above were aqueous stable above the optimum salinity. The ultralow IFT windows obtained using the novel surfactants were in between that of the conventional surfactants discussed above.

FIGS. 26-30 show additional phase behavior results, as follows:

TABLE 3

Figure 26:
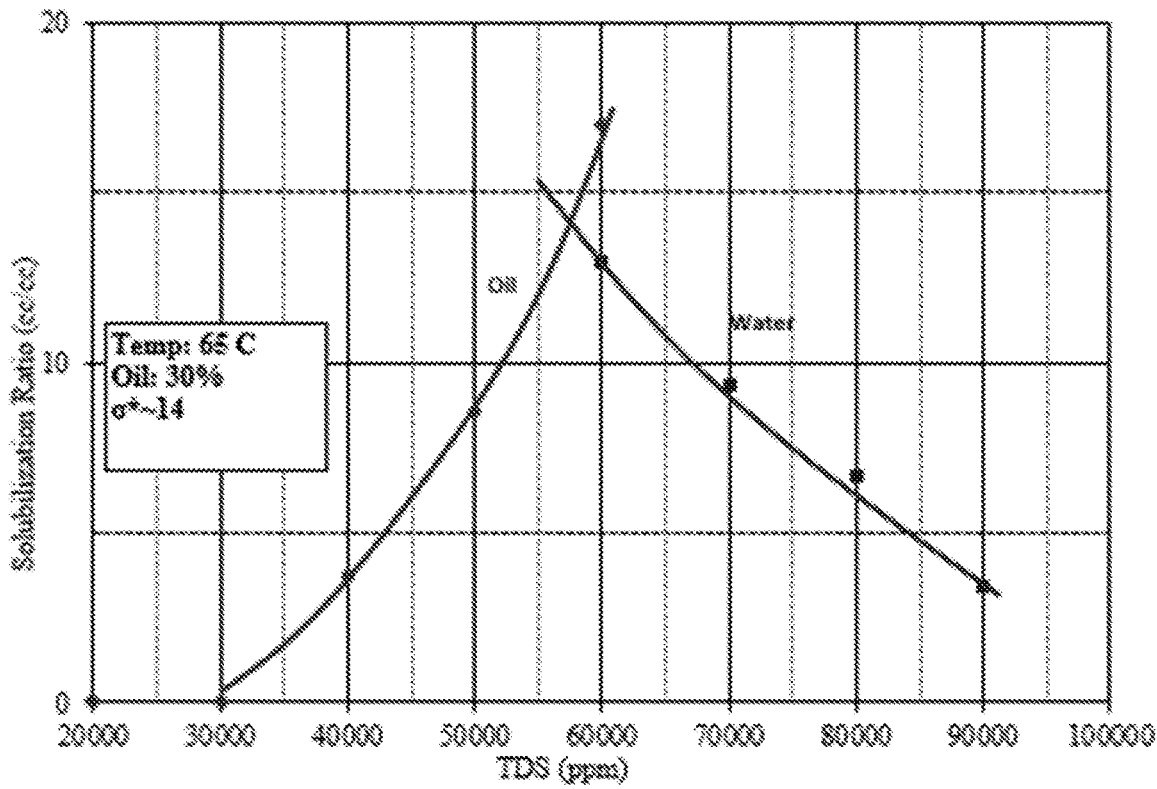
FIG. 26 depicts solubilization ratios for phase behavior tubes of 0.5% 2EH—O-40PO-40EO—$COO^-$, 0.5% $C_{19-23}$ IOS, 1% TEGBE 65° C.
Figure 27:
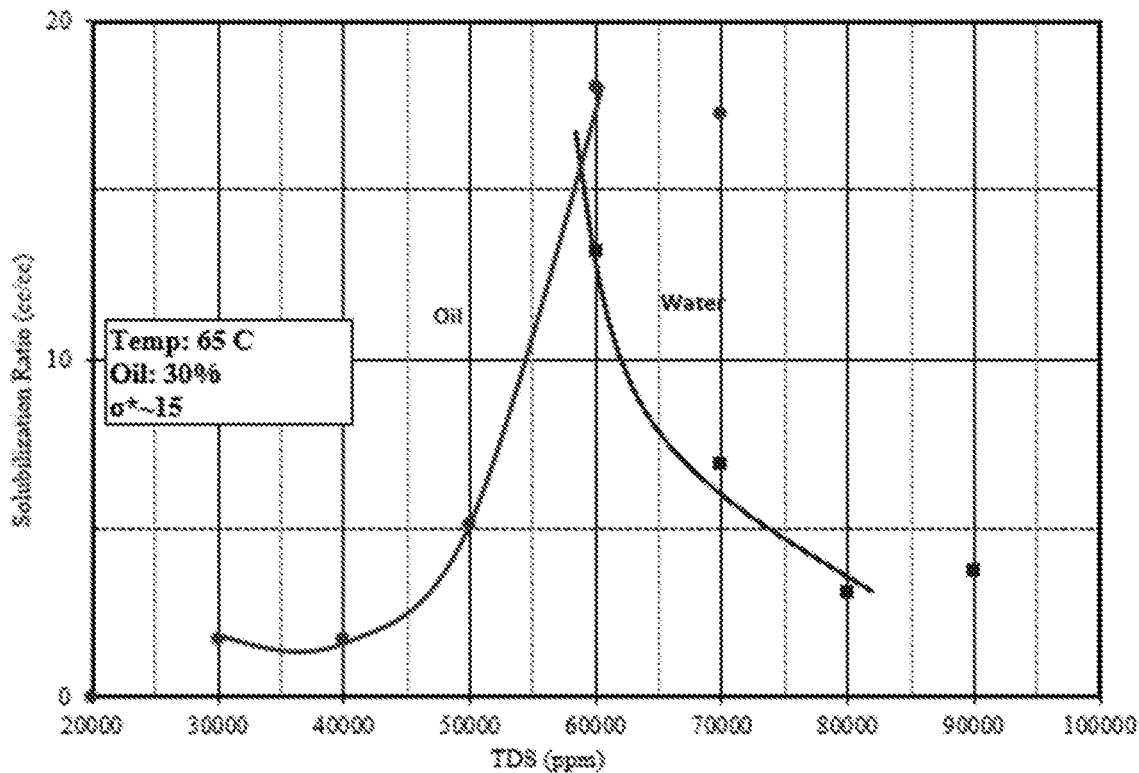
FIG. 27 depicts solubilization ratios for phase behavior tubes of 0.5% 2EH—O-40PO-40EO, 0.5% $C_{19-23}$ MS, 1% TEGBE 65° C.
Figure 28:
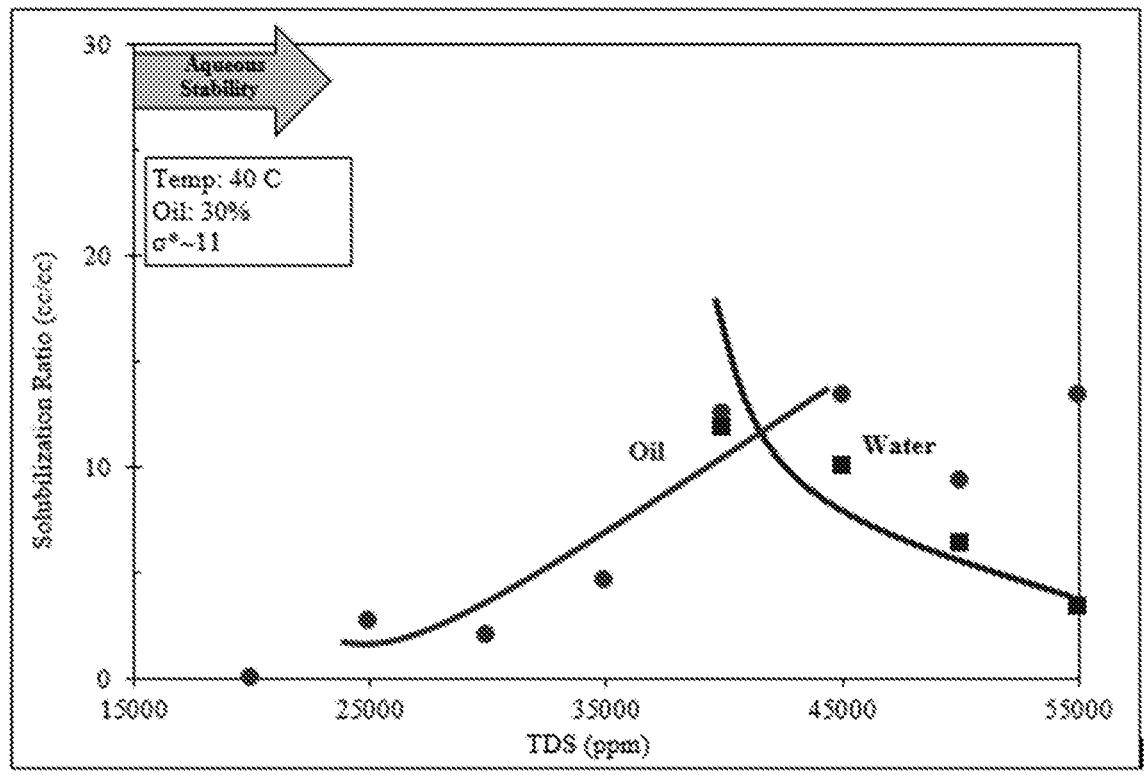
FIG. 28 depicts solubilization ratios for phase behavior tubes of 0.5% $CH_3$—O-21PO—$SO_4$, 0.5% $C_{15-18}$ MS.
Figure 29:
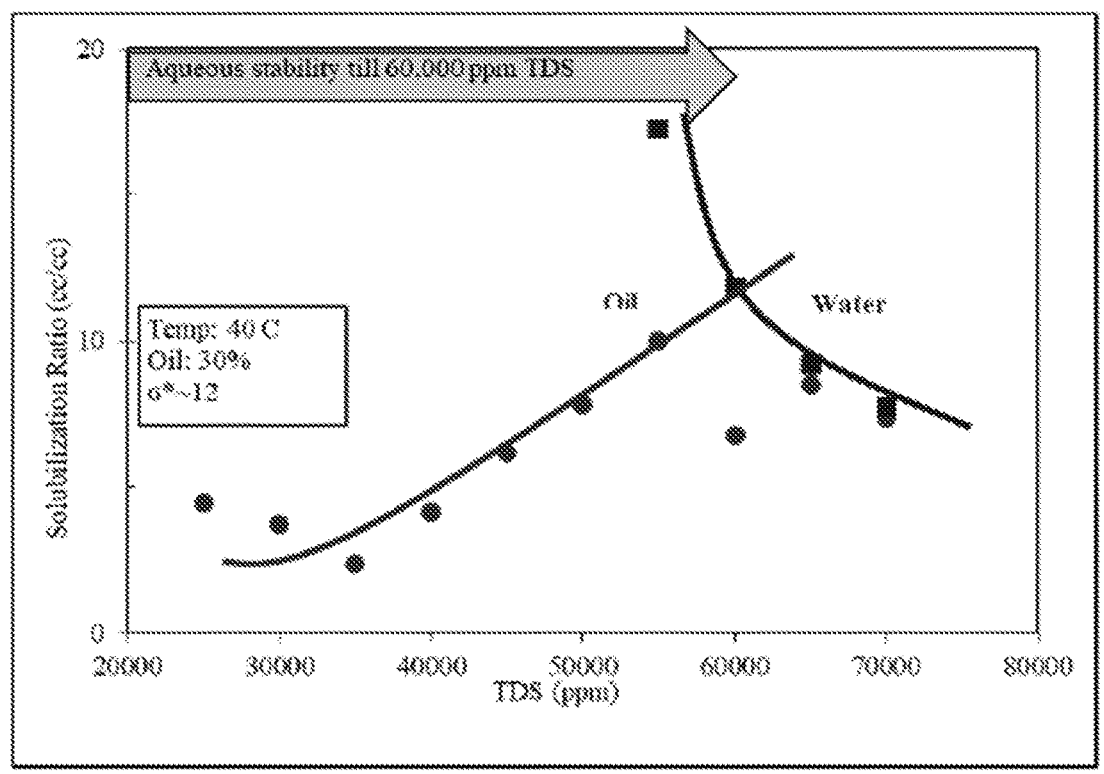
FIG. 29 depicts solubilization ratios for phase behavior tubes of 0.5% $CH_3$—O-21PO-10EO-$SO^0$, 0.5% $C_{15-18}$ MS.
Figure 30:
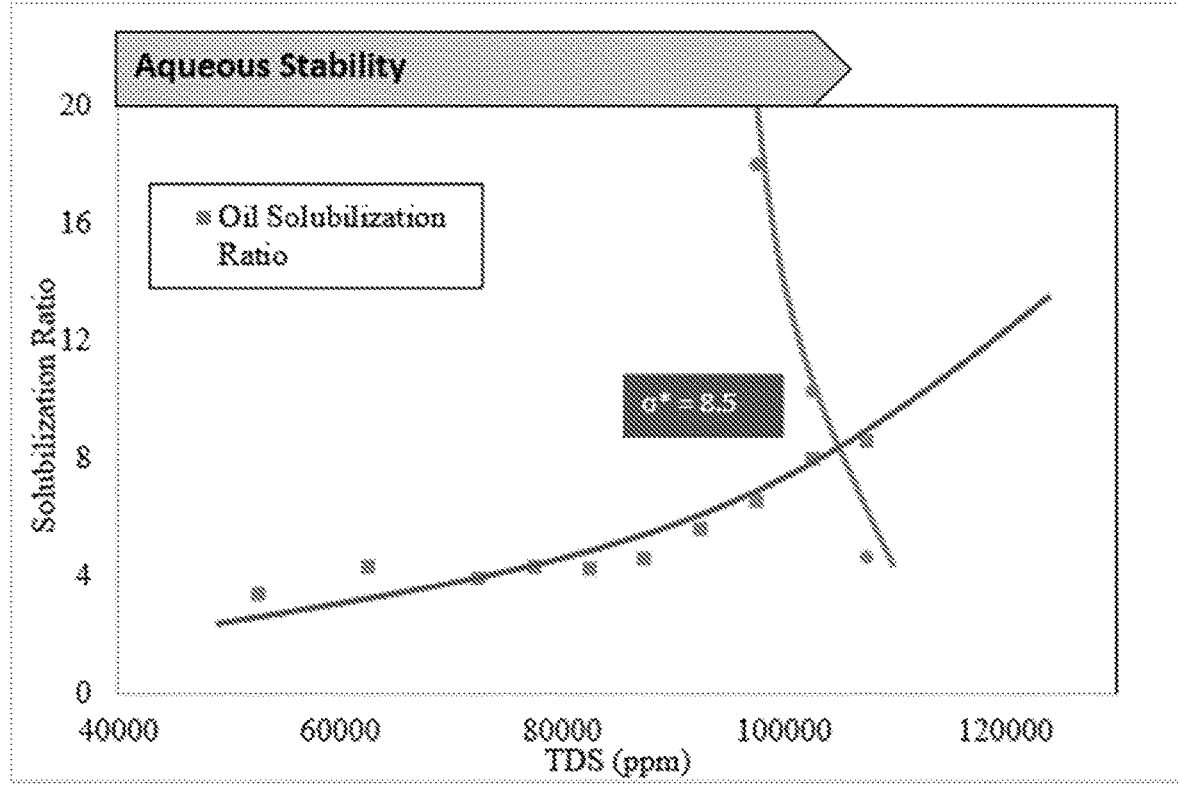
FIG. 30 depicts solubilization ratios for phase behavior tubes of 0.5% 2EH—O-60PO-60EO—$COO^-$, 0.5% $C_{15-18}$ MS.

| FIGS. 26-30. | |
|---|---|
| FIG. 26 | Solubilization ratios for phase behavior tubes 0.5% 2EH-O-40PO-40EO-COO—, 0.5% $C_{19-23}$ IOS, 1% TEGBE 65 C. |
| FIG. 27 | Solubilization ratios for phase behavior tubes 0.5% 2EH-O-40PO-40EOH 0.5% $C_{19-23}$ IOS, 1% TEGBE 65 C. |
| FIG. 28 | Solubilization ratios for phase behavior tubes 0.5% $CH_3$—O-21PO-$SO_4$, 0.5% $C_{15-18}$ IOS |
| FIG. 29 | Solubilization ratios for phase behavior tubes 0.5% $CH_3$—O-21PO-10EO-$SO_4$, 0.5% $C_{15-18}$ IOS |
| FIG. 30 | Solubilization ratios for phase behavior tubes 0.5% 2EH-O-60PO-60EO-COO$^-$, 0.5% $C_{15-18}$ IOS |

Figure 31:
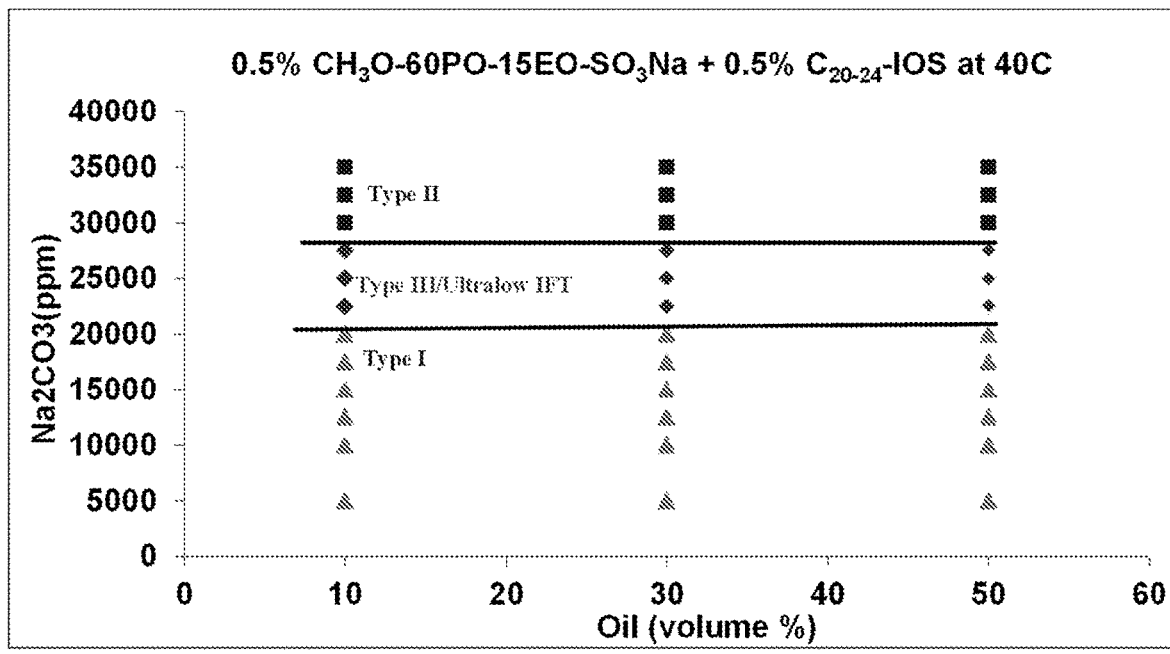
FIG. 31 depicts alkali surfactant phase behavior results for $CH_3$—O-60PO-15EO—$SO_3Na$, 0.5% $C_{20-24}$ MS.

Surfactant phase behavior experiments were performed for developing alkali surfactant phase (ASP) floods using the blend of $CH_3$-x(PO)-y(EO)—$SO_4$ surfactant with IOS surfactants. The results shown in FIG. 31 were obtained with a blend of 0.5% $CH_3$-60(PO)-15(EO)—$SO_4$ and 0.5% $C_{20-24}$ IOS, and an inactive crude oil of 5 cP at 40° C. Sodium carbonate was used as the alkali in these scans. FIG. 31 shows the ultralow IFT region using this formulation for 10%, 30% and 50% oil (by volume). Ultralow IFT was observed between 2.25-2.75% $Na_2CO_3$ in these formulations. The formulation was found to be aqueous stable at these conditions. A typical Winsor type phase behavior was observed from the surfactant phase behavior tubes. Surfactant polymer (SP) formulation was similarly developed for the same crude oil using the same surfactant blend. The optimum salinity for this formulation was found to be about 2.5% NaCl.

Example 4

Oil Recovery Corefloods

Oil recovery corefloods were conducted in Boise and Berea sandstone cores to test the ultralow IFT surfactant formulations in terms of their effectiveness in improving oil recovery from waterflooded oil reservoirs. A 1 ft long and 1.5-inch diameter cylindrical core was dried (at 80° C.) and placed in a coreholder. An overburden pressure of about 1000 psi was applied; air porosity and air permeability were obtained. A vacuum was then applied to remove the air from the core. A desired initial oil saturation, typically 80-85%, was obtained by injecting a given amount of brine followed by the oil. This method of achieving the initial oil saturation is also known as vacuum saturation method. Oil was injected at different flow rates to obtain the oil permeability at the reservoir temperature. This was followed by a waterflood at 1 ft/d. The brine injection rate was then increased up to 10 ft/d to remove any capillary end effects. The injection rate was varied to measure water relative permeability at residual oil saturation. The end point relative permeabilities of oil and water were used to estimate the polymer requirement in the surfactant flood. Surfactant flood, followed by polymer injection, was then performed at 1 ft/d and effluent samples were collected. The pressure drop across the core was recorded. The effluent samples were analyzed for oil recovery (visually), surfactant concentration (by HPLC), polymer viscosity (by rheometer) and salinity (by refractometer).

Figure 32:
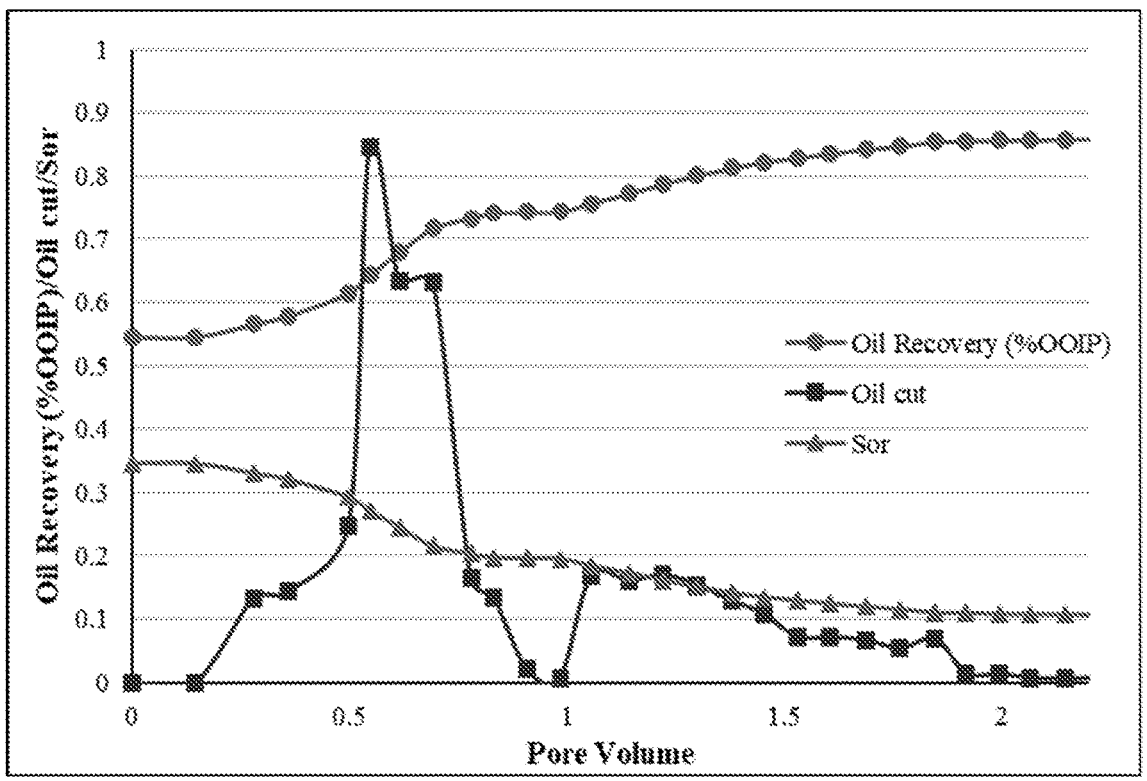
FIG. 32 depicts surfactant polymer oil recovery coreflood results conducted in a Boise sandstone core for 0.5 wt % $CH_3O$-21PO-10EO—$SO_4$ and 0.5 wt % $C_{20-24}$ IOS.

The results of coreflood C1 are shown in FIG. 32. The properties of the core are given in Table 4. The injection scheme for this coreflood is given in Table 5.

TABLE 4

Properties of the cores used in oil recovery corefloods

|  | SP coreflood C1 | SP coreflood C2 |
| --- | --- | --- |
| Core | Boise Sandstone | Berea Sandstone |
| Diameter(cm) × Length (cm) | 3.7 × 29.9 | 3.7 × 29.6 |
| Porosity (%) | 28 | 21.0 |
| Permeability (md) | 900 | 220 |

TABLE 5

Injections scheme in corefloods C1 and C2

|  | SP coreflood C1 | SP coreflood C2 |
| --- | --- | --- |
| SP/ASP slug | 0.3 PV<br>0.5 wt % $CH_3O$-21PO-10EO-sulfate + 0.5 wt % $C_{20-24}$ IOS<br>1.5 wt % NaCl<br>3250 ppm FP 3330S | 0.3 PV<br>0.5 wt % $CH_3O$-21PO-10EO-sulfate + 0.5 wt % $C_{19-23}$ IOS<br>4.5 wt % NaCl<br>3500 ppm FP 3330S |
| Polymer drive 1 | 0.3 PV<br>3.5 wt % NaCl<br>3500 ppm FP 3330S | 2 PV<br>2.5 wt % NaCl<br>3500 ppm FP 3330S |
| Polymer drive 2 | 1.5 PV<br>1.5 wt % NaCl<br>3500 ppm FP 3330S | n.a. |

The core was waterflooded with 5 wt % NaCl brine, which resulted in a residual oil saturation of about 34.6%. 0.3 PV of SP slug was injected followed by 0.3 PV of polymer drive 1 and 1.5 PV of polymer drive 2 at 1 ft/d. The SP slug was injected based on the surfactant phase behavior obtained from prior experiments. Note that the surfactant formulation consisted of 0.5 wt % $CH_3O$-21PO-10EO-sulfate and 0.5 wt % $C_{20-24}$ IOS. The ultralow IFT region was observed at around 3.5 wt % NaCl at 40° C. The surfactant solution was, however, aqueous stable only up to 1.5 wt % NaCl at 40° C. As a result, the injection scheme shown in Table 5 was used. The core was waterflooded with the formation brine, corresponding to Winsor type II region in phase behavior B3. The SP slug was injected at 1.5 wt % NaCl, which corresponds to salinity in Winsor type I region, since this was the aqueous stability limit of this surfactant formulation. The idea was to obtain the ultralow IFT region due to the mixing of SP slug with the formation brine. The SP slug was followed up with polymer drive I prepared in 3.5 wt % NaCl. The idea was to again increase the salinity at the end of the SP slug into type III region due to mixing. The last polymer slug was prepared in 1.5 wt % NaCl, corresponding to Winsor type I region. The oil recovery results obtained from this coreflood is shown in FIG. 32. The oil recovery increased from about 54% OOIP (after waterflood) to about 85% OOIP after the SP flood. The residual oil saturation lowered from about 34% to about 10% and a good oil bank was observed.

Figure 33:
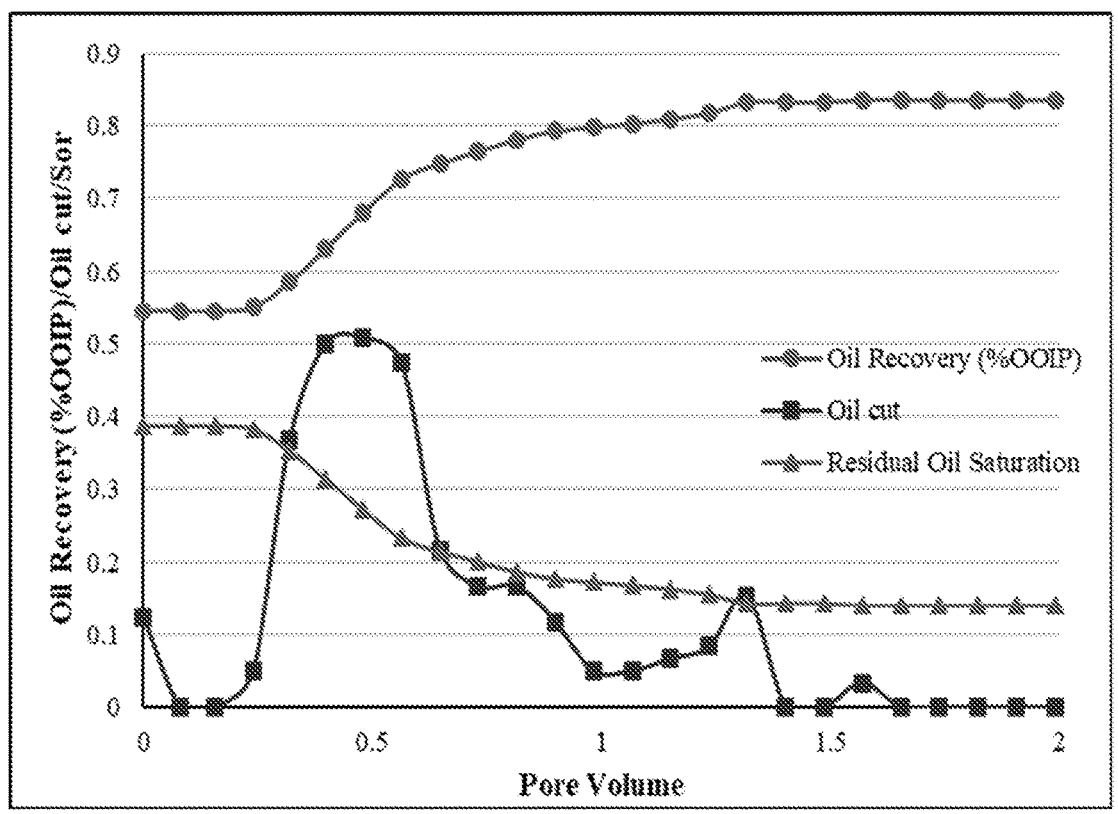
FIG. 33 depicts surfactant polymer oil recovery coreflood results conducted in a Berea sandstone core for 0.5 wt % $CH_3O$-21PO-10EO—$SO_4$, 0.5 wt % $C_{19-23}$ IOS and 1 wt % TEGBE.

The surfactant formulation used in the previous coreflood was not aqueous stable at the optimum salinity. Therefore, an improved surfactant formulation was developed. In this formulation, $C_{20-24}$ IOS was replaced with $C_{16-23}$ IOS. Ultralow IFT from this formulation was observed at around 4.5 wt % NaCl. The surfactant formulation was aqueous stable at this salinity. Another SP coreflood (coreflood C2) was conducted in a Berea sandstone core using this formulation at 40° C. The core was waterflooded with 7 wt % NaCl brine after which 0.4 PV of SP slug was injected at 1 ft/d. 2 PV of polymer drive was injected next. The injection scheme used in this coreflood is given in Table 5. The oil recovery results obtained from this coreflood are shown in Figure. 33. The coreflood resulted in increasing the oil recovery from about 54% OOIP to about 83% OOIP. The oil saturation was lowered from about 39% to about 14%. Note that although a good oil bank was observed in this coreflood, the oil cut dropped earlier than expected, possibly due to a steep salinity gradient.

Example 5

Foam Behavior and Hardness Tolerance

Figure 34:
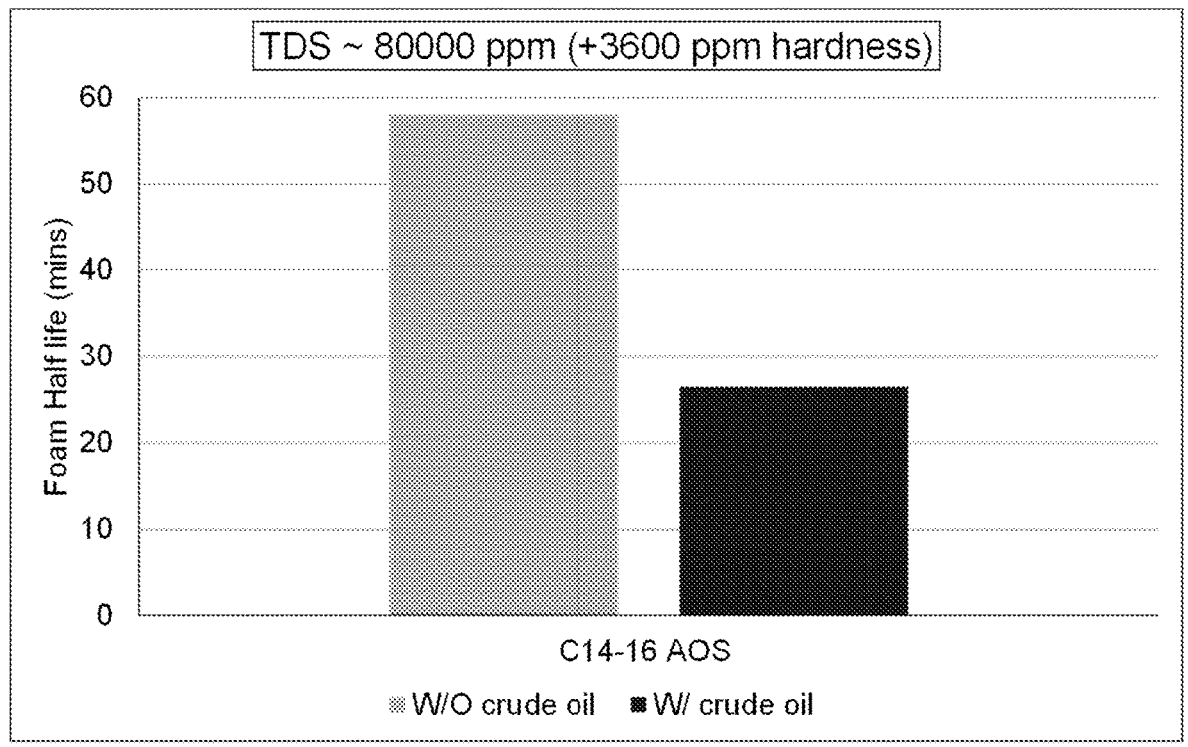
FIG. 34 depicts effect of crude oil on foam half-life with AS-40 at high salinity.

For foam applications, bulk foam studies were performed to qualitatively estimate the foaming ability and foam stability of the different surfactant formulations. Equal amounts of oil and aqueous solutions were used. $C_{14-16}$ AOS, a commonly used foaming surfactant, showed good foaming up to the salinity of 80,000 ppm at 100 deg C. However, poor aqueous stability was observed above 80,000 ppm in the presence of crude oil. (See FIG. 34).

Figure 35:
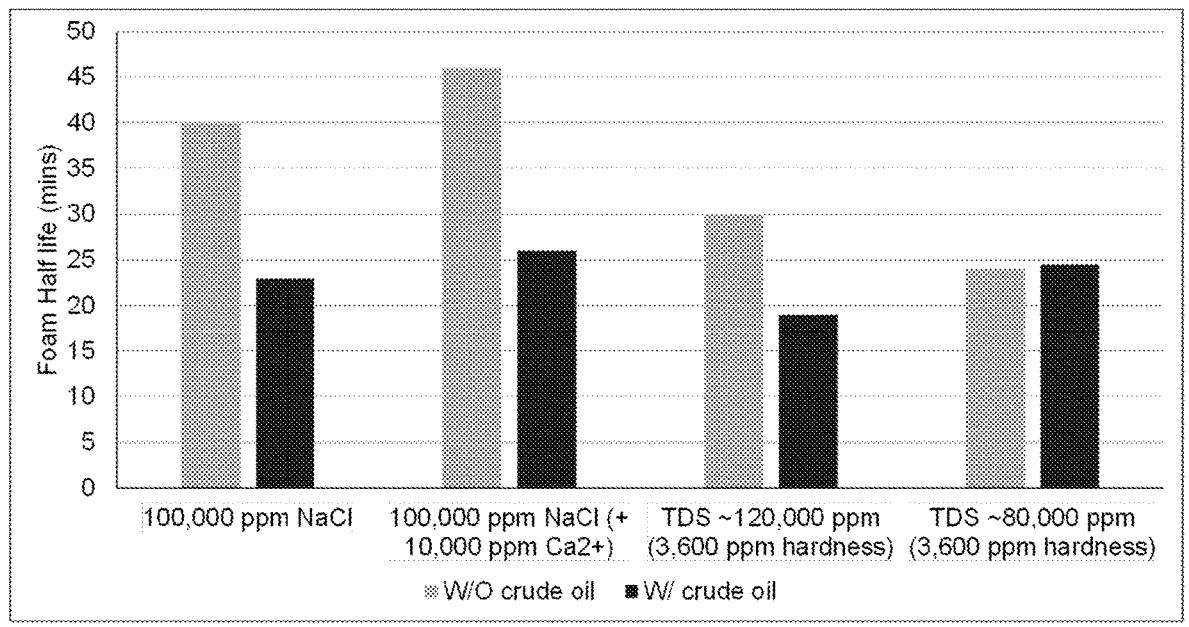
FIG. 35 depicts effect of crude oil on foam half-life with 0.5% $C_{14-16}$ AOS, 0.5% $CH_3$—O-60PO-20EO—$SO_4Na$.

At elevated salinities (>=100000 ppm), $C_{14-16}$ AOS in synergy with $CH_3$-x(PO)-y(EO)—$SO_4$ surfactants showed good foaming abilities and aqueous stability. No negative impact of crude oil on foam half-life was observed with surfactants containing $CH_3$-x(PO)-y(EO)—$SO_4$ which shows that this surfactant blend has better compatibility with crude oil compared to $C_{14-16}$ AOS by itself. FIG. 35 shows the summary of bulk foam stability tests performed at 60° C. The detrimental effect of crude oil was observed at higher salinities, only.

The surfactants of the present invention were blended with AS-40, as set forth in Table 6.

TABLE 6

Surfactant Formulations

| Surfactant Type | Surfactant Formulation | HLB | Viscosity (cP) (25° C.) |
| --- | --- | --- | --- |
| Blend A | 0.5% $C_{14-16}$ AOS + 0.5% $CH_3O$-60PO-20EO-$SO_3Na$ | 6.714 | 1.12 |
| Blend B | 0.5% $C_{14-16}$ AOS + 0.5% $CH_3O$-60PO-15EO-$SO_3Na$ | 6.655 | 1.15 |
| Blend C | 0.5% $C_{14-16}$ AOS + 0.5% $CH_3O$-21PO-$SO_3Na$ | 5.921 | 1.25 |
| AS-40 | 1% $C_{14-16}$ AOS | 6.867 | 2.0 |

Figure 36:
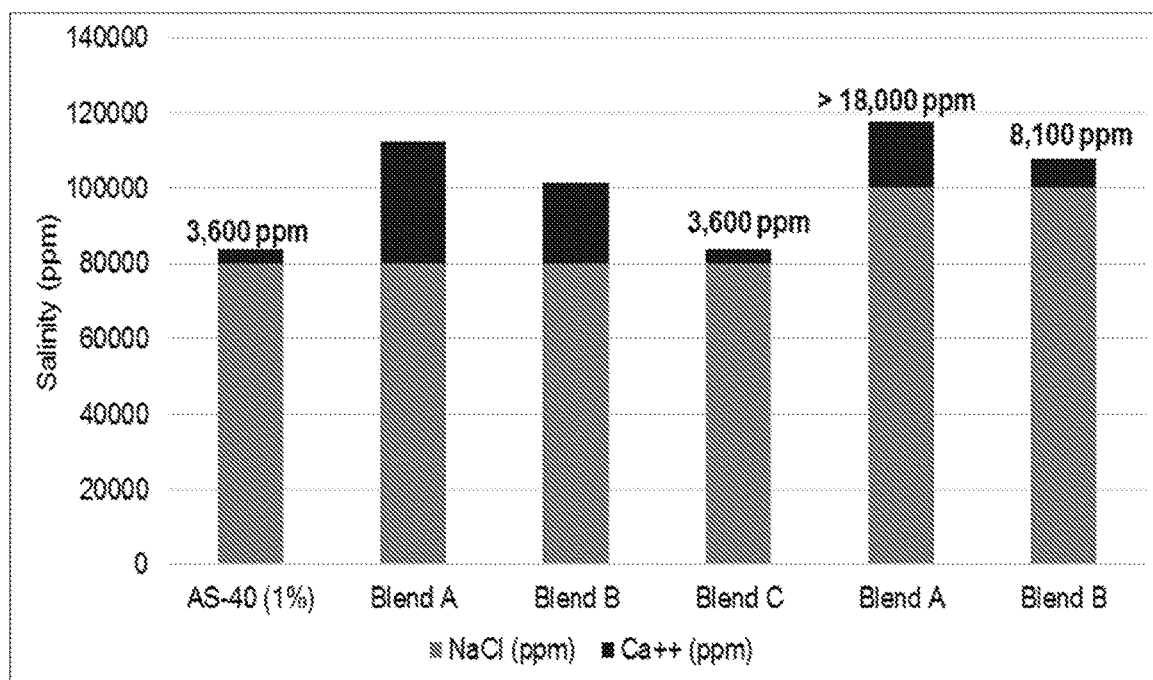
FIG. 36 depicts hardness tolerance for AS-40 and surfactant blends.

The surfactants of the present invention demonstrated increased critical hardness limits when blended with AS-40, as shown in FIG. 36.

Example 6

Viscoelastic Behavior

Figure 37:
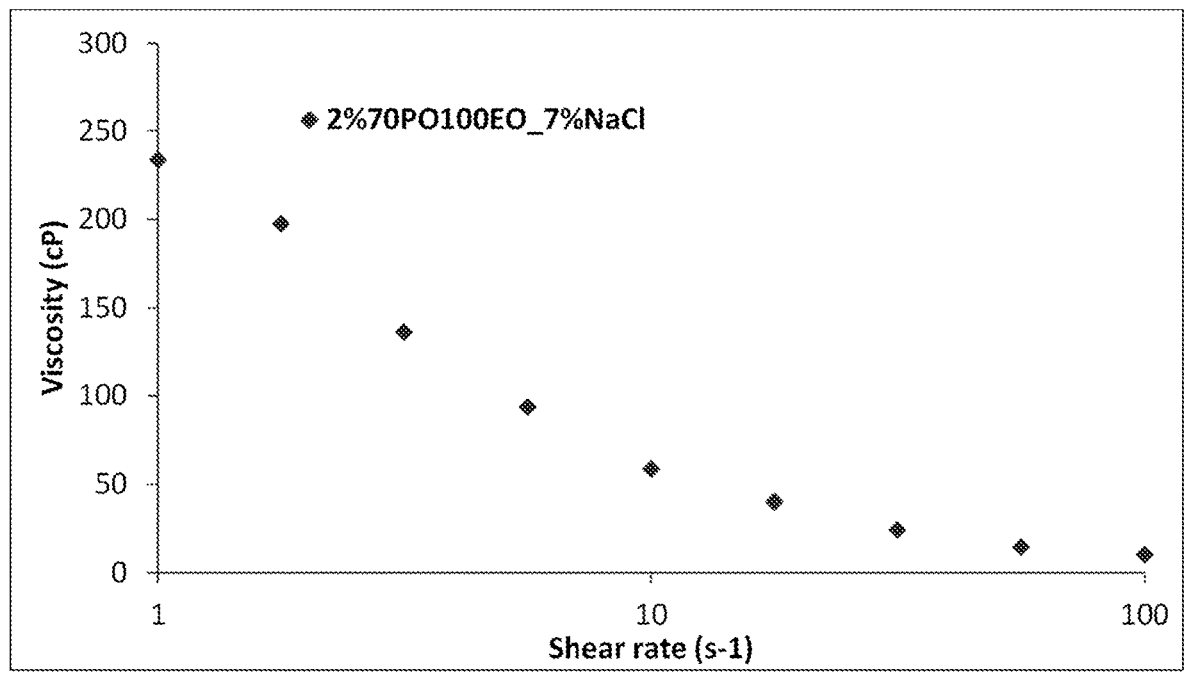
FIG. 37 depicts Stability of cylindrical micelles of 2% $CH_3$—O-70PO-100EO.
Figure 38:
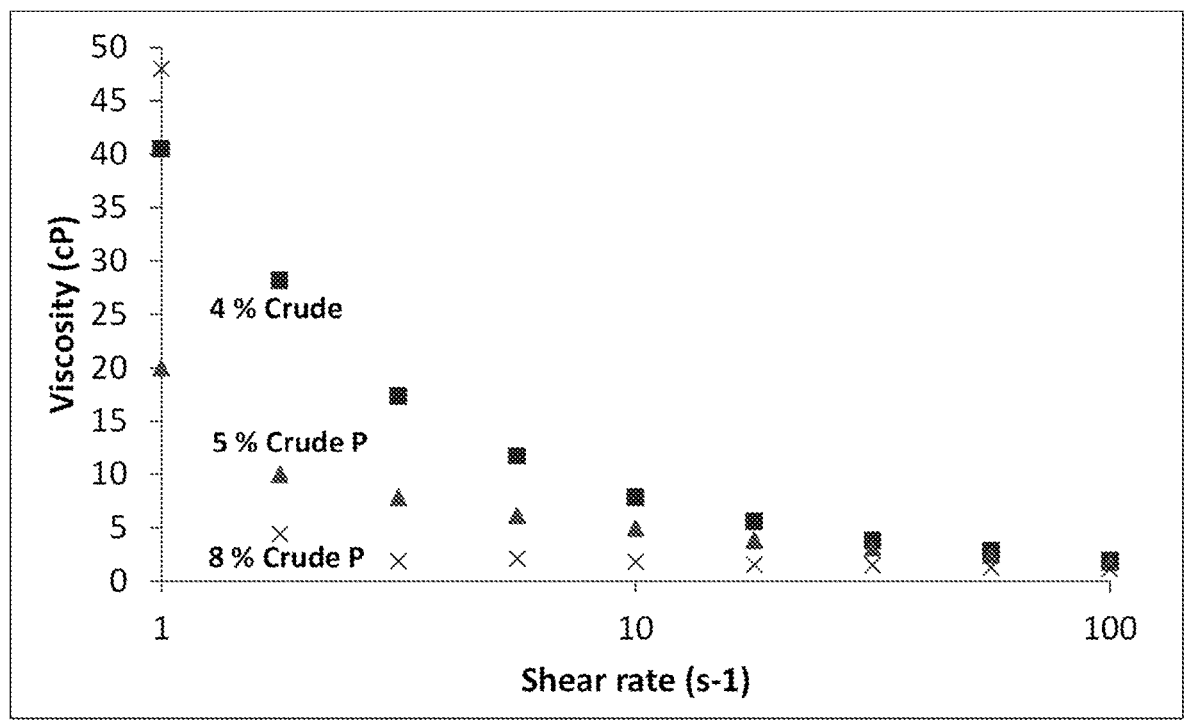
FIG. 38 depicts stability of micelles in presence of crude oil P of 2% $CH_3$—O-70PO-100EO.
Figure 39:
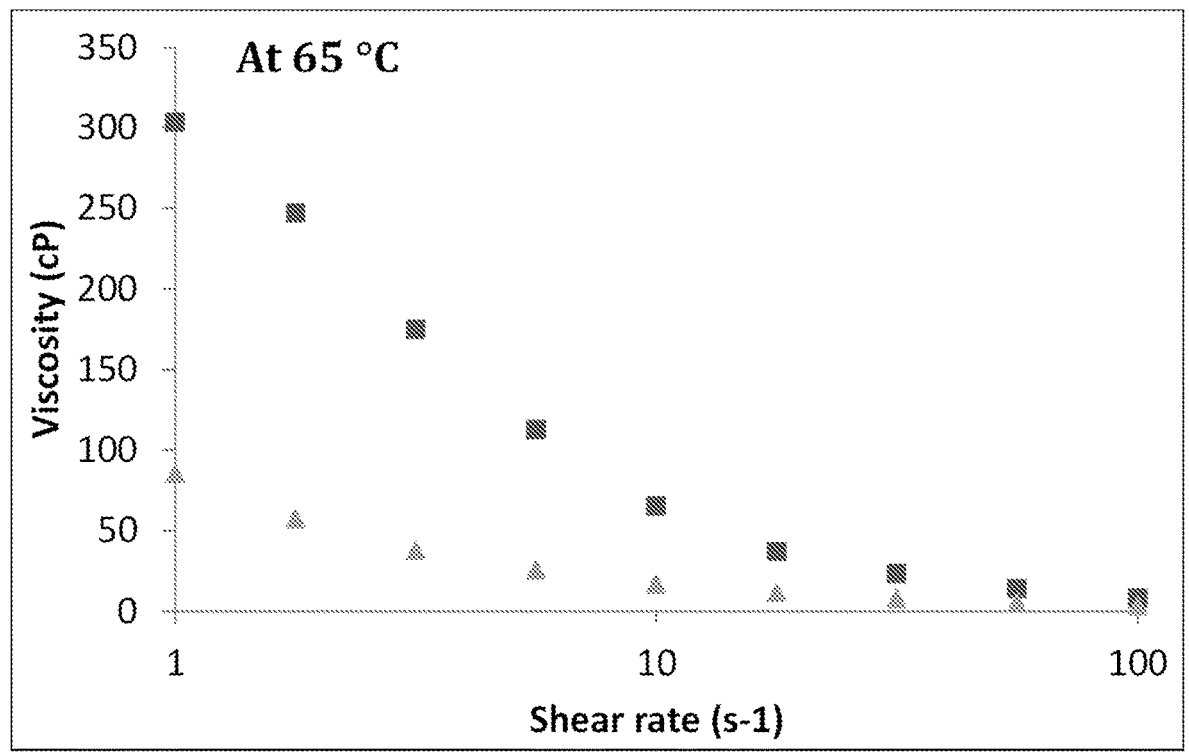
FIG. 39 depicts stability of micelles in presence of crude oil K of 2% $CH_3$—O-70PO-100EO.
Figure 40:
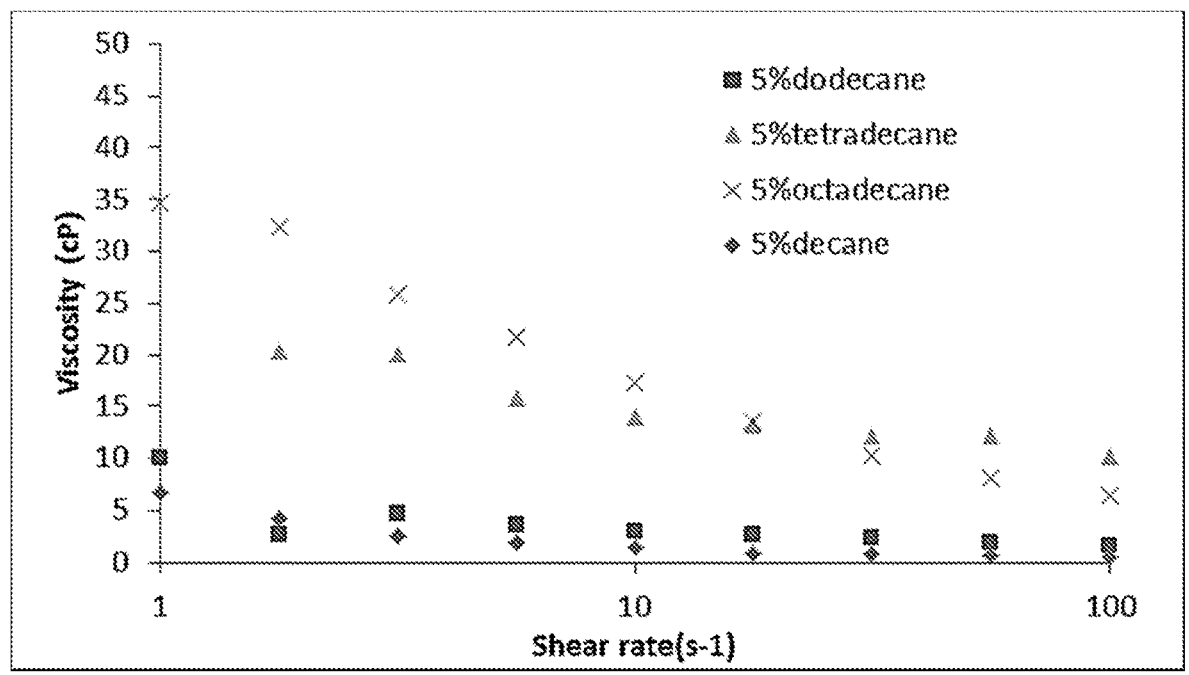
FIG. 40 depicts stability of micelles in presence of alkanes of 2% $CH_3$—O-70PO-100EO.

Viscoelastic behavior was measured for 2% $CH_3$—O-70PO-100EOH. Under favorable salinity and temperature, the surfactant forms cylindrical micelles and the solution becomes viscous. Without any salinity, the solution is viscous around 110° C., and with very high concentrated salt solution (~25% NaCl) the solution is viscous at room temperature. The viscosity at 7% NaCl at 65° C. is shown in FIG. 37. The 2% surfactant solution in 7% NaCl was mixed with crude oil P, K and alkanes and occasionally shaken. The viscosity was measured after two days, as shown in FIG. 38, FIG. 39, and FIG. 40, respectively.

From the foregoing it will be seen that this invention is one well adapted to attain all ends and objectives hereinabove set forth, together with the other advantages which are obvious and which are inherent to the invention.

Since many possible embodiments may be made of the invention without departing from the scope thereof, it is to be understood that all matters herein set forth or shown in the accompanying drawings are to be interpreted as illustrative, and not in a limiting sense.

While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

We claim:

1. A compound having the formula:

$$R^1-O-(PO_x\text{-}EO_y)-Z$$

wherein $R^1$ is a branched $C_3$ to $C_7$ alkyl;
wherein x is 15-100;
wherein y is 10-250;
wherein (x+y)≥25; and
wherein Z is carboxylate.

2. The compound of claim 1, wherein $R^1$ is selected from the group consisting of isopropyl, isobutyl, t-butyl, sec-butyl, and their isomers.

3. The compound of claim 2, wherein $R^1$ is isobutyl, t-butyl, or sec-butyl.

4. The compound of claim 1, wherein $R^1$ is methylpentyl.

5. The compound of claim 1, wherein y is an integer from 65 to 105.

6. The compound of claim 5, wherein x is greater than or equal to y.

7. An aqueous composition comprising the compound of claim 1 and a co-surfactant.

8. An emulsion comprising the aqueous composition of claim 7 and a hydrocarbon material.

9. A method of using the compound of claim 1 in an enhanced oil recovery method comprising:
contacting a hydrocarbon with the compound of claim 1, wherein said hydrocarbon is in contact with a solid material in a petroleum reservoir; and
allowing said hydrocarbon material to separate from the solid material.

10. A method of using the compound of claim 1 in household, institutional or industrial cleaning comprising:
contacting a household, institutional or industrial surface with the compound of claim 1.

11. A compound having the formula:

$$R^1-O-(PO_x\text{-}EO_y)-Z$$

wherein $R^1$ is $C_1$, $C_2$, or a branched $C_3$ or $C_4$ alkyl;
wherein x is 15-100;
wherein y is 10-250;
wherein (x+y)≥25; and
wherein Z is carboxylate.

12. A compound having the formula:

$$R^1-O-(PO_x\text{-}EO_y)-Z$$

wherein $R^1$ is a branched $C_5$ to $C_8$;
wherein x is 15-100;
wherein y is 10-250;
wherein (x+y)≥25; and
wherein Z is carboxylate.

13. An aqueous composition comprising the compound of claim 11 and a co-surfactant.

14. A method of using the compound of claim 11 in an enhanced oil recovery method comprising:
contacting a hydrocarbon with the compound of claim 11, wherein said hydrocarbon is in contact with a solid material in a petroleum reservoir; and
allowing said hydrocarbon material to separate from the solid material.

15. An aqueous composition comprising the compound of claim 12 and a co-surfactant.

16. A method of using the compound of claim 12 in an enhanced oil recovery method comprising:
contacting a hydrocarbon with the compound of claim 12, wherein said hydrocarbon is in contact with a solid material in a petroleum reservoir; and
allowing said hydrocarbon material to separate from the solid material.

17. An emulsion comprising the aqueous composition of claim 13 and a hydrocarbon material.

18. An emulsion comprising the aqueous composition of claim 15 and a hydrocarbon material.

* * * * *